United States Patent
Mitsuhashi et al.

(10) Patent No.: US 7,922,991 B2
(45) Date of Patent: Apr. 12, 2011

(54) BASIC MAGNESIUM CARBONATE, PRODUCTION METHOD AND USE OF THE SAME

(75) Inventors: Kohei Mitsuhashi, Nishitama-gun (JP); Katsuyuki Tanabe, Nishitama-gun (JP); Naoki Tagami, Nishitama-gun (JP)

(73) Assignee: Nittetsu Mining Co., Ltd., Tokyo (JP)

( * ) Notice: Subject to any disclaimer, the term of this patent is extended or adjusted under 35 U.S.C. 154(b) by 841 days.

(21) Appl. No.: 10/504,567

(22) PCT Filed: Feb. 12, 2003

(86) PCT No.: PCT/JP03/01437
§ 371 (c)(1),
(2), (4) Date: Aug. 13, 2004

(87) PCT Pub. No.: WO03/068681
PCT Pub. Date: Aug. 21, 2003

(65) Prior Publication Data
US 2005/0129606 A1    Jun. 16, 2005

(30) Foreign Application Priority Data

Feb. 13, 2002 (JP) .............................. P. 2002-035110
May 24, 2002 (JP) .............................. P.2002-150377
Jun. 20, 2002 (JP) .............................. P.2002-179462
Jul. 30, 2002 (JP) .............................. P. 2002-220768
Sep. 17, 2002 (JP) .............................. P. 2002-269777

(51) Int. Cl.
*C01F 5/24* (2006.01)
*D21C 3/02* (2006.01)

(52) U.S. Cl. .......................................... 423/430; 162/90
(58) Field of Classification Search .................. 423/430, 423/431, 432, 421; 162/90
See application file for complete search history.

(56) References Cited

U.S. PATENT DOCUMENTS 3,723,596 A * 3/1973 Lecuit et al. .................. 423/430

FOREIGN PATENT DOCUMENTS

| GB | 2089334 | * | 2/1980 |
|---|---|---|---|
| JP | 32-632 B1 | | 1/1957 |
| JP | 54-80298 A | | 6/1979 |
| JP | 58-161918 A | | 9/1983 |
| JP | 60-46921 A | | 3/1985 |
| JP | 60046921 | * | 3/1985 |
| JP | 63-258642 A | | 10/1988 |
| JP | 2-208220 A | | 8/1990 |

OTHER PUBLICATIONS

Fukuhara et al., Synthesis of tubes of a magnesium-rich carbonate and of its oxide decomposition products, 1998, Journal of American Ceramic Society, 81 (10), 2746-48.*
International Search Report, dated Apr. 1, 2003.

* cited by examiner

*Primary Examiner* — Stanley Silverman
*Assistant Examiner* — James A Fiorito
(74) *Attorney, Agent, or Firm* — Sughrue Mion, PLLC

(57) ABSTRACT

Basic magnesium carbonate comprising a tubular aggregated particle of flaky fine crystals.

31 Claims, 4 Drawing Sheets

10μm

1μm

1μm

1μm

BASIC MAGNESIUM CARBONATE, PRODUCTION METHOD AND USE OF THE SAME

TECHNICAL FIELD

The present invention relates to a basic magnesium carbonate having a novel and specific shape and a method for producing the same, and a filler for low density paper, low density paper, a hollow carrier, a functional particle, a composition or a structure and the like containing the basic magnesium carbonate. More particularly, the present invention relates to basic magnesium carbonate comprising an aggregated particle of a novel and specific shape of flaky fine crystals and a method for producing the same, and a filler for low density paper which affects changes into the low density and high rigidity of paper, and low density paper containing the filler, a hollow carrier in which a tubular structure of the basic magnesium carbonate is utilized, and a functional particle which comprises encapsulating an active ingredient within the carrier, a composition or a structure, comprising the basic magnesium carbonate.

BACKGROUND ART

A basic magnesium carbonate that has been industrially utilized is represented by the chemical formula of $mMgCO_3 \cdot Mg(OH)_2 \cdot nH_2O$. The value represented by m and n in this chemical formula varies depending on the condition of the production, and thus is not constant. It is common that m is 3 to 5, and n is 3 to 8.

The basic magnesium carbonate is usually obtained as amorphous aggregated particles of flaky fine crystals, having characteristics that a bulk density is as low as 0.2 to 0.3 g/mL, and a specific surface area is comparatively high and is 10 to 40 $m^2/g$.

Basic magnesium carbonate has been utilized in the field such as rubbers, paints, paper manufacturing, medicinal products, cosmetics, building materials and ceramic materials through taking advantages of the characteristics as described above. Particularly, as a filler for a rubber, it has characteristics such as imparting transparency to a compounded natural rubber and improving the strength of a rubber.

As the method of producing a basic magnesium carbonate, there are many methods such as a soda ash method in which a reaction of a soluble magnesium salt such as magnesium chloride with sodium carbonate is utilized, an ammonium carbonate method in which a reaction of a soluble magnesium salt with ammonium carbonate is utilized, and a gas method in which a reaction of magnesium hydroxide with a carbon dioxide gas is utilized. In any one of these methods, production of a basic magnesium carbonate is allowed by a maturation for a long period of time of a normal magnesium carbonate (represented by the chemical formula of $MgCO_3 \cdot nH_2O$, wherein n is 3, in general) or magnesium bicarbonate ($Mg(HCO_3)_2$) obtained as an intermediate product by a reaction of a magnesium source with a carbonate source.

Investigation and development regarding the basic magnesium carbonate have been carried out since a long time ago. For example, a method for producing a basic magnesium carbonate having an excellent performance as a filler for use in a rubber within a short time through maturation of a suspension containing normal magnesium carbonate under an appropriate condition of the temperature was proposed in Japanese Patent No. 1207124, and a method for producing a basic magnesium carbonate having an excellent performance as a filler for use in a synthetic resin by a reaction of a water soluble magnesium source with a water soluble carbonate salt in the presence of a water soluble sulfate salt was proposed in JP-A-61-31314.

Further, a basic magnesium carbonate having a particular amount of oil absorption and specific surface area which is obtained by heating an aqueous solution of magnesium bicarbonate while circulation was proposed in JP-A-2-208220; and a basic magnesium carbonate exhibiting a particular X-ray diffraction pattern obtained by heating a suspension of normal magnesium carbonate in the coexistence of hydroxycarboxylic acid was proposed in JP-A-3-97618. Moreover, as the publications in which attention was focused on particle shape of a basic magnesium carbonate, there are Japanese Patent Nos. 1635418 and 2602444, where a basic magnesium carbonate in the form of a spherical porous particle formed by aggregation of primary particles, and which exhibits a feature such as a particular bulk density and a specific surface area was proposed.

DISCLOSURE OF THE INVENTION

As described above, although a lot of studies have been carried out of a basic magnesium carbonate, under present circumstances, use thereof is still limited only to restricted fields such as fillers for a rubber and the like. In addition, also with regard to the particle shape, only amorphous or spherical ones have been known which comprise flaky fine crystals, and the performance and use thereof is still far from enough satisfaction. Thus, a basic magnesium carbonate having a novel shape capable of dealing with the expansion of use to other field, the improvement of a performance, the improvement of a function and the like has been desired.

Taking into account of such circumstances, in order to expand the use, improve the performance and the function of a basic magnesium carbonate, the inventors of the present invention attempted to synthesize a basic magnesium carbonate exhibiting a novel characteristic by controlling the shape of its particle. Thus, they elaborately investigated, and succeeded in the development to accomplish the present invention. Accordingly, an object of the present invention is to provide a basic magnesium carbonate having a novel shape and exhibiting a variety of excellent characteristics derived from the shape, and a method of producing the same, as well as a filler for low density paper, low density paper, a hollow carrier, a functional particle, a composition or a structure containing the basic magnesium carbonate and exhibiting a variety of excellent characteristics on behalf of the characteristic and the like of the basic magnesium carbonate.

The present invention provides a basic magnesium carbonate and a method of producing the same, and a composition and a structure containing the basic magnesium carbonate in order to solve the problem as described above. Among them, the basic magnesium carbonate has a novel shape being a tubular aggregated particle of flaky fine crystals.

The basic magnesium carbonate which is a tubular aggregated particle of flaky fine crystals of the present invention has a novel shape as described above, and the flaky fine crystals forming this aggregated particle has a thickness of 0.005 to 0.5 μm and a diameter of 0.1 to 10 μm (indicating the distance across at the longest part). An aggregate of these flaky fine crystals in the form of a card house structure is the basic magnesium carbonate of the present invention.

There are two examples of methods for producing the basic magnesium carbonate having the novel structure according to the present invention.

The first method (S method) comprises a first step for producing a columnar particle of a normal magnesium carbonate and a second step for producing a basic magnesium carbonate comprising a tubular aggregated particle by subjecting the normal magnesium carbonate produced in the first step to a heat treatment, wherein it is required that the first step is carried out at a temperature of 20 to 60° C., and that the second step is carried out at a temperature of 35 to 80° C., with the proviso that the temperature in the second step is a temperature that is higher than the temperature in the first step.

The second method (G method) comprises a first step for preparing a solution of magnesium hydrogen carbonate by introducing a gas containing carbon dioxide in a suspension of magnesium hydroxide, a second step for producing a columnar particle of a normal magnesium carbonate by adjusting a pH range of the solution of magnesium hydrogen carbonate to be 7.5 to 11.0, and a third step for producing a basic magnesium carbonate by adjusting a pH range and a temperature of a suspension of the columnar particles of the normal magnesium carbonate to be 9.0 to 12.0 and 30 to 75° C., followed by keeping the temperature within the range.

The basic magnesium carbonate of the present invention has a variety of excellent characteristics such as high specific surface area, high pore volume, high oil absorbing property, high water absorbing property and low bulk density on behalf of the unique shape which is porous and tubular. Therefore, by including the basic magnesium carbonate in any of various compositions or structures such as rubbers, resins, paper, formed products, medical or agricultural drugs and cosmetics, it is possible to impart the characteristics as described above to each of the various products, which are the composition or structure of the present invention.

Furthermore, the filler for paper containing the basic magnesium carbonate of the present invention not only can change the paper into the low density more efficiently on behalf of the aforementioned characteristics of the basic magnesium carbonate, but have the effect to improve the rigidity of the paper, which is the filler for low density paper of the present invention. In addition, the paper containing the filler is the low density paper of the present invention, which has a characteristic of being highly rigid accompanied by the characteristic of low density.

Moreover, because the basic magnesium carbonate has a hollow structure which is tubular, it is also excellent in a characteristic as a carrier, which carrier is the hollow carrier of the present invention. In addition, a particle, which is encapsulating an active ingredient within the hollow carrier, which have a characteristic such as a sustained release property, a masking property or a release-controlling property is the functional particle of the present invention.

BEST MODE FOR CARRYING OUT THE INVENTION

Figure 1:
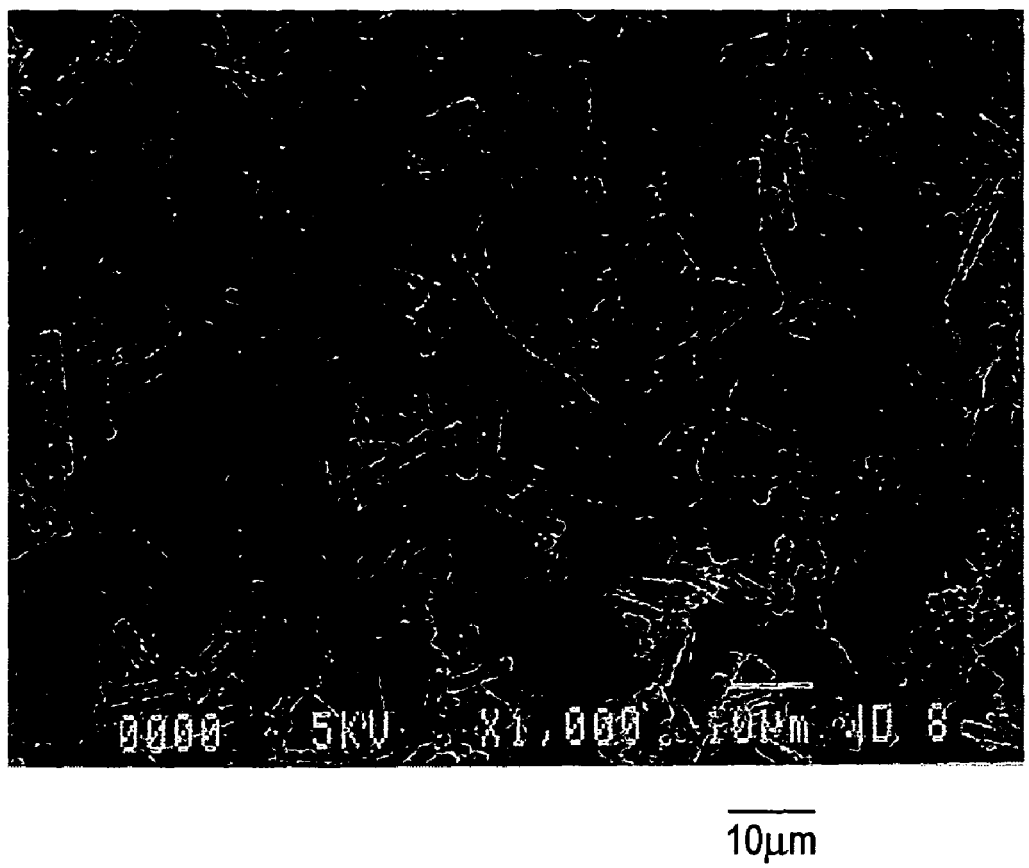
FIG. 1 is an SEM photograph (×1,000) showing the particle shape of the basic magnesium carbonate comprising a tubular aggregated particle of flaky fine crystals obtained in Example 1.
Figure 2:
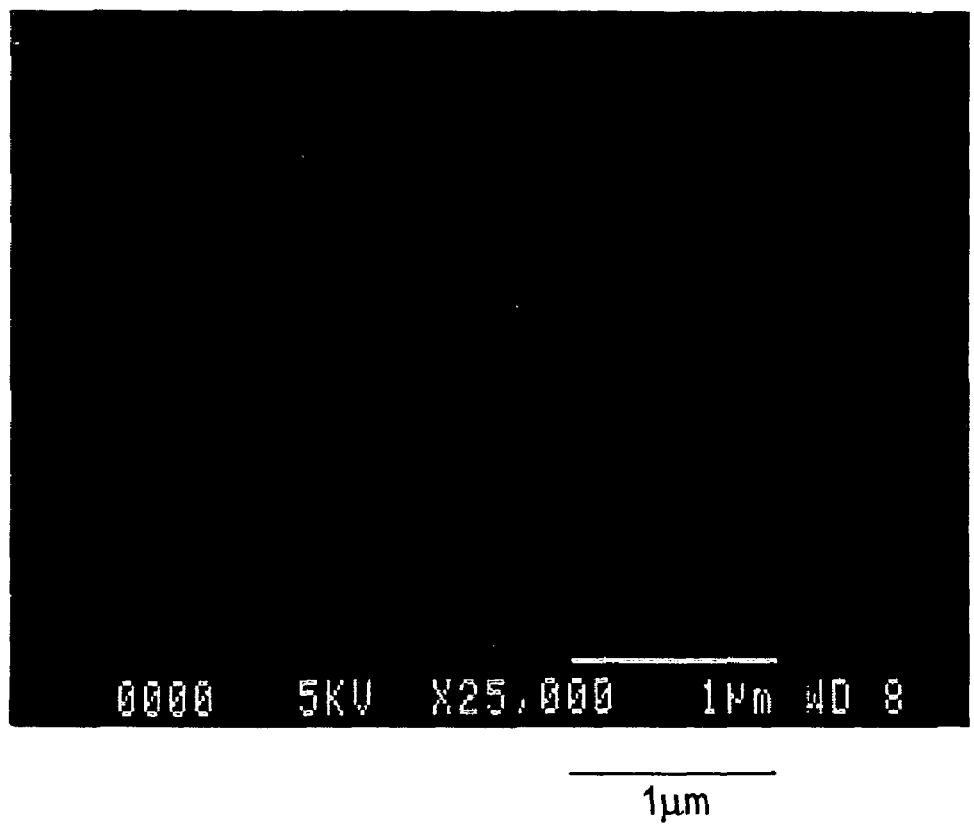
FIG. 2 is an SEM photograph (×25,000) showing the particle shape of the basic magnesium carbonate which is a tubular aggregated particle of flaky fine crystals obtained in Example 1.
Figure 3:
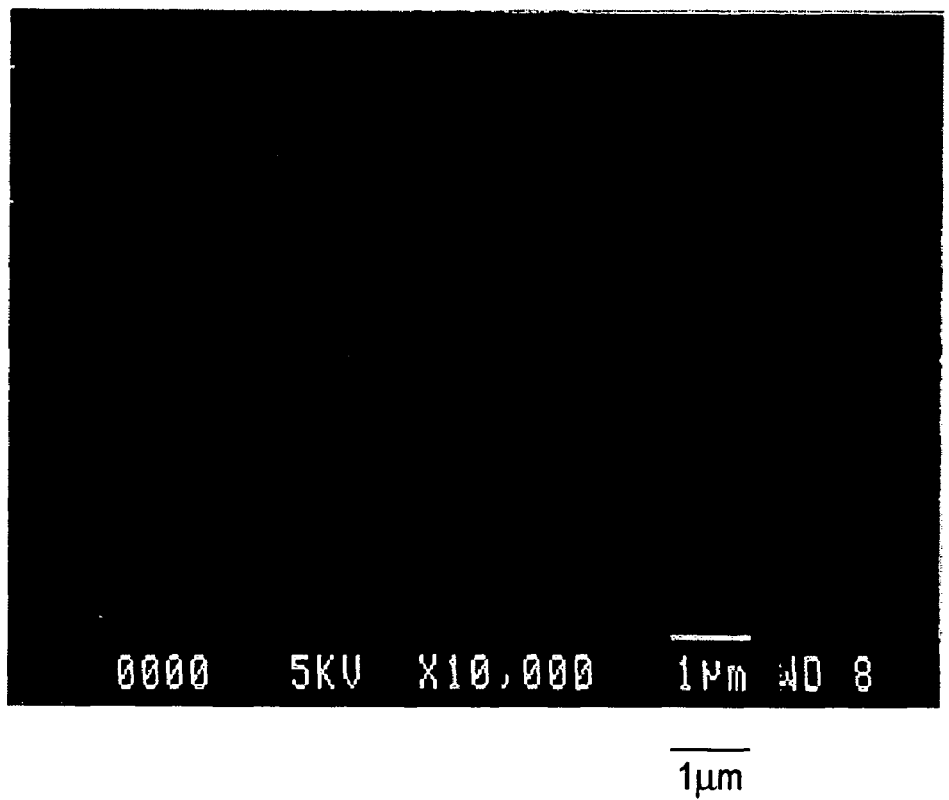
FIG. 3 is an SEM photograph (×10,000) showing the particle shape of the basic magnesium carbonate which is a tubular aggregated particle of flaky fine crystals obtained in Example 5.
Figure 4:
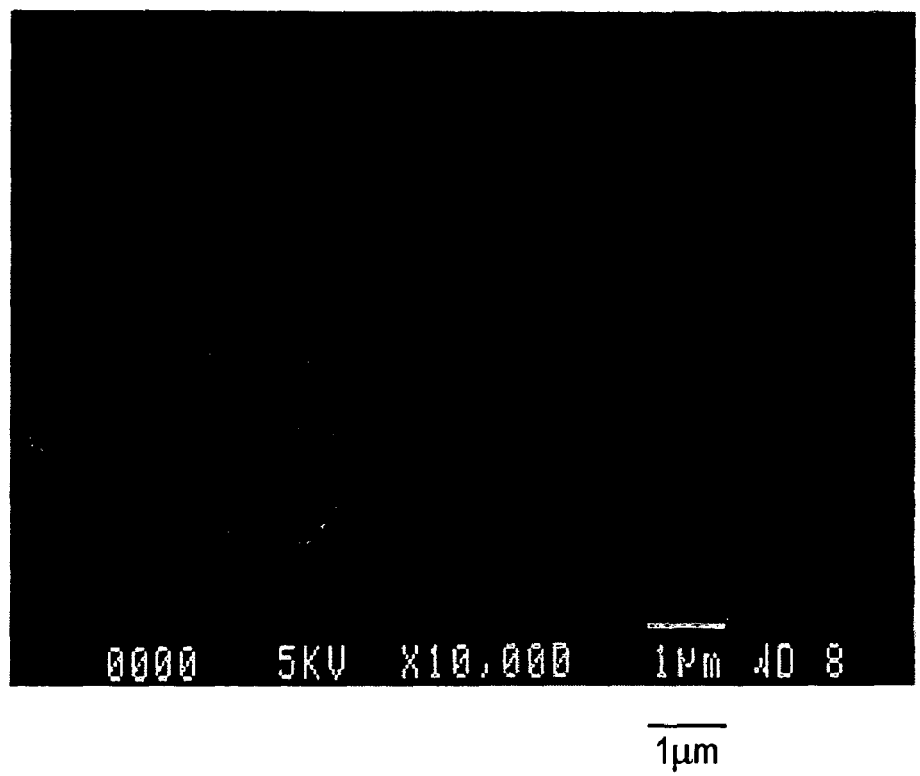
FIG. 4 is an SEM photograph (×10,000) showing the particle shape of the basic magnesium carbonate which is a tubular aggregated particle of flaky fine crystals obtained in Example 6.

Hereinafter, best mode for carrying out the present invention is explained in detail, however, it would be obvious that the present invention is not anyhow limited thereby, but is specified by the description of claims.

The present invention provides a basic magnesium carbonate having a novel shape and a method for producing the same, as well as a composition, or a structure or the like containing the basic magnesium carbonate. The basic magnesium carbonate of the present invention exhibits a specific shape that is a tubular aggregated particle of flaky fine crystals, and the flaky fine crystal forming this aggregated particle has a thickness of 0.005 to 0.5 µm and a diameter of 0.1 to 10 µm. An aggregate of these flaky fine crystals assembled in the form of a card house structure is the basic magnesium carbonate of the present invention.

The basic magnesium carbonate referred to herein is represented by the chemical formula of $mMgCO_3 \cdot Mg(OH)_2 \cdot nH_2O$, wherein the value represented by m and n is not particularly limited, which may be the value of m being 3 to 5, and the value of n being 3 to 8, as in generally known basic magnesium carbonate.

The tubular aggregated particle of the basic magnesium carbonate of the present invention is not an aggregate in which the flaky fine crystals is easily dispersed, which depends on the changes in the environment such as simple stirring, the temperature or the pH, but which is physically fixed through assembling of the flaky fine crystals of basic magnesium carbonate, although the precise mechanism is unclear.

According to the basic magnesium carbonate, a variety of excellent effects are brought about on behalf of the unique particle shape that is tubular comprising the flaky fine crystals. Specifically, on behalf of the shape that is tubular having a stretching property, it exerts a reinforcing effect as a filler for a resin, a rubber or the like. Furthermore, on behalf of the irregularity on the surface of the particle resulting from being an aggregated particle of flaky fine crystals, adhesiveness to a matrix substance is improved when it is utilized as any of various fillers. In addition, on behalf of being an aggregated particle in the form of a card house structure, it is also excellent in the performance as a porous material, thereby being effective also as various adsorbents, carriers and the like.

Moreover, it is desired that the basic magnesium carbonate comprising a tubular aggregated particle has a shape of the internal diameter of 0.5 to 5 µm, the external diameter of 1 to 20 µm, the ratio of internal diameter/external diameter of 0.1 to 0.95, the length of 5 to 200 µm, and the ratio of length/external diameter of 2 to 50 and preferably the ratio of length/external diameter of 4 to 50. Accordingly, the characteristics as described above are efficiently exhibited.

Furthermore, on behalf of the unique shape which is tubular, bulk density as powder is reduced, and thus, an effect is exerted in weight saving of the product when it is used as any of various fillers. In addition thereto, it is excellent in an adiabatic property due to increased voids. Furthermore, the space within the tube can be utilized as a field of a reaction for the synthesis of a fine vessel or a fine particle, or it can be also utilized for the synthesis of a microtube in which the tubular structure used as a template. Moreover, because it has a hollow structure that is tubular, it is also effective as a carrier which internally includes an active ingredient within the tubular structure thereof.

It is desired that the basic magnesium carbonate comprising a tubular aggregated particle of the present invention has a specific surface area according to a BET method of 70 to 200 $m^2/g$, preferably 85 to 200 $m^2/g$, more preferably 90 to 200 $m^2/g$, or preferably pores in which a pore diameter of 0.01 to 100 μm has a pore volume (A) of 5000 to 12000 $mm^3/g$, and the ratio B/A which is a ratio to the pore volume (B) of pores having a pore diameter of 0.5 to 5 μm is 0.45 to 0.85 in the porosimetry as measured by a mercury porosimetry. It is desired both of the specific surface area and pore volume fall within the range described above, thereby exhibiting the characteristics more efficiently which are derived from the shape that is tubular.

The inventors of the present invention suppose that such a specific surface area and a porosimetry are derived from the unique shape that is tubular. More specifically, it is believed that on behalf of the shape of tubular, a surface is generated also on the interior wall of the tube, and thus, the specific surface area is increased. In addition, it is also believed that by setting the internal diameter of the tube of 0.5 to 5 μm, the ratio of the pore volume of the pores having a diameter of 0.5 to 5 μm is increased, in particular.

With regard to the shape of tubular, according to the observation with SEM and TEM, end faces of respective flaky fine crystals are present dependently on the external surface, however, to the contrary, the interior surface of the tube is in a comparatively smooth state without clear findings of the presence of end faces of respective flaky fine crystals as on the external surface. Also, there exist not only those having opened both ends of the tube, but also those having a shape with closed ends.

Next, the method for producing the basic magnesium carbonate comprising a tubular aggregated particle of flaky fine crystals of the present invention is described. There are two methods of the production of the present invention (S method, G method) as described above.

The first method (hereinafter, referred to as S method) comprises a first step for producing a columnar particle of a normal magnesium carbonate at a temperature of 20 to 60° C. by mixing a water soluble magnesium salt and a water soluble carbonate salt in an aqueous solution, and a second step in which a suspension of the columnar particles of the normal magnesium carbonate is subjected to a heat treatment at a temperature that is higher than the temperature in the production of the normal magnesium carbonate in the first step, and at a temperature of 35 to 80° C. On behalf of the presence of these two steps, the basic magnesium carbonate comprising a tubular aggregated particle of flaky fine crystals can be produced.

The water soluble magnesium salt used in this first step may be any one of various water soluble magnesium salts, which may be used without particular limitation. Illustrative examples thereof include magnesium chloride, magnesium sulfate, magnesium nitrate, magnesium acetate or the like. As the water soluble magnesium salt, a solution containing magnesium sulfate which is generated in the desulfurization and neutralization step according to a magnesium hydroxide method can be also utilized, which is preferred also in light of effective utilization of an industrial by-product.

The desulfurization and neutralization step according to the magnesium hydroxide method referred to herein is a step of eliminating sulfur oxide, which is included in an exhaust gas yielded during coal firing or the like, by allowing a reaction with magnesium hydroxide, or a step for neutralizing waste sulfuric acid with magnesium hydroxide. Accordingly, a solution containing magnesium sulfate is generated as a by-product in the step. Although the solution containing magnesium sulfate is currently discharged into the oceans as wastewater, effective utilization thereof has been desired in view of the global environmental preservation or resource recycling.

Also, with regard to the water soluble carbonate salt, any one of various water soluble carbonate salts can be used without particular limitation, similarly to the magnesium salt. Illustrative examples thereof include sodium carbonate, potassium carbonate, ammonium carbonate and the like. As the water soluble carbonate salt, sodium carbonate, potassium carbonate, ammonium carbonate or the like produced by introducing and allowing absorption of a carbon dioxide gas into an aqueous solution of an alkaline substance such as sodium hydroxide, potassium hydroxide or aqueous ammonia may be also used. In particular, according to the method, a carbon dioxide gas included in the exhaust gas or the like can be utilized as a carbonate source, therefore, it is effective in reduction of the amount of emission of the carbon dioxide gas.

In the first step, the aforementioned water soluble magnesium salt and a water soluble carbonate salt are allowed to react in an aqueous solution, thereby permitting precipitation of the columnar particle of the normal magnesium carbonate as an intermediate product. Methods of the precipitation may include such as a method in which an aqueous magnesium chloride solution is added to an aqueous sodium carbonate solution and a method in which ammonium carbonate is added into an aqueous magnesium sulfate solution and may be a condition as far as a reaction of a magnesium ion with a carbonate ion is occured through mixing a water soluble magnesium salt and a water soluble carbonate salt in a solution. The reaction then is preferably carried out with stirring of the reaction liquid for the purpose of keeping the uniformity of the reaction.

Concentration of the water soluble magnesium and the water soluble carbonate salt used in the first step is not particularly limited, but may be selected ad libitum taking into account of the amount of the normal magnesium carbonate to be produced. Desirably, the concentration is adjusted to such that solid content in the suspension of normal magnesium carbonate becomes 10 to 300 g/L. When the content is less than 10 g/L, production efficiency may be impaired. When the content is greater than 300 g/L, viscosity of the suspension becomes so high that it may be hard to be stirred, thereby involving difficulty in carrying out the reaction uniformly and efficiently.

Furthermore, with regard to ratio of the amount of the water soluble magnesium salt to the water soluble carbonate salt, it is preferred that the molar ratio of magnesium (Mg):carbonic acid ($CO_3$) is 1:0.7 to 1:2.0, and preferably 1:0.8 to 1:1.8. Then the normal magnesium carbonate can be efficiently produced by adjusting the ratio to fall within the range. When the ratio is out of the range, excessively existing water soluble magnesium salt or water soluble carbonate salt is wasted, which is not economically favorable. Additionally, an adverse influence may be exerted when the tubular basic magnesium carbonate is produced in the second step.

The shape of the normal magnesium carbonate produced in the first step is required to be columnar, and it is preferable that the diameter thereof is 0.5 to 10 μm, the length is 5 to 500 μm, and the ratio of length/diameter is 2 to 500. When the diameter, the length and the ratio of length/diameter are set to be within the aforementioned range, a tubular aggregated particle of the basic magnesium carbonate which is more excellent in powder characteristics such as specific surface area, porosimetry and bulk density can be obtained efficiently in the following second step.

Moreover, in cases of the normal magnesium carbonate having the shape other than that described above, time required for production of the basic magnesium carbonate in the second step may be extremely long, thereby lowering the producing efficiency, or the objective tubular particle may not be obtained. The normal magnesium carbonate produced in the first step is a hydrate of magnesium carbonate represented by the chemical formula of $MgCO_3 \cdot nH_2O$, wherein n is 3 in general, but any one in which n is other than 3 is also permitted without limitation as long as it has the shape as described above.

The basic magnesium carbonate of the present invention is believed to form the unique shape that is tubular through the production of the flaky fine crystals of the basic magnesium carbonate from the surface of the columnar particle of the normal magnesium carbonate. It is thus speculated that the shape of the normal magnesium carbonate which is an intermediate product greatly affects the shape of the basic magnesium carbonate that is a final product. Therefore, it is important that normal magnesium carbonate having a suitable shape, desirably having a diameter of 0.5 to 10 μm, a length of 5 to 500 μm, and a ratio of length/diameter of 2 to 500 by regulating the condition for the production of the normal magnesium carbonate which is an intermediate product, depending on the shape, particularly diameter and length of the objective basic magnesium carbonate.

Accordingly, in order to produce a columnar particle of the normal magnesium carbonate by which the tubular basic magnesium carbonate having the objective shape is obtained efficiently in the second step, it is required that the temperature for the reaction of the water soluble magnesium salt with the water soluble carbonate salt in an aqueous solution is set to be within the range of 20 to 60° C. When the reaction temperature is lower than 20° C., it is not practical due to extremely reduced production rate of the normal magnesium carbonate that is an intermediate product, thereby reducing the production efficiency. To the contrary, when the reaction temperature is higher than 60° C., the object of the present invention cannot be achieved because the normal magnesium carbonate of the objective shape cannot be obtained, or the tubular basic magnesium carbonate cannot be obtained in the following second step.

Furthermore, when control of the shape of the tubular aggregated particle of the basic magnesium carbonate produced in the second step is desired through regulating the shape of the normal magnesium carbonate produced in the first step, the shape of the normal magnesium carbonate can be regulated by controlling the reaction condition of the first step ad libitum. For example, with regard to the diameter of the columnar particle of the normal magnesium carbonate, when temperature in production of the normal magnesium carbonate is comparatively higher, the columnar particle has a smaller diameter. With regard to the pH, when pH at the initiation of the production of the normal magnesium carbonate in the first step is comparatively higher, the columnar particle of the normal magnesium carbonate of a smaller diameter can be produced.

Although the suspension of the columnar particles of the normal magnesium carbonate thus obtained in the first step may be directly subjected to the second step, in instances where recovery of an anionic component of the soluble magnesium salt or a cationic component of the soluble carbonate salt dissolved in the suspension as an impurity is intended, or in instances where remanence of these impurities in the normal magnesium carbonate which is a final product is not preferred, elimination of the impurity may be carried out through substituting the liquid with water or the like.

Subsequently, in the second step, the suspension of the columnar particles of the normal magnesium carbonate obtained in the first step is subjected to a heat treatment at 35 to 80° C., and at a temperature that is higher than the temperature in the first step to produce the basic magnesium carbonate. It is important that the temperature for the heat treatment in the second step is set to be a temperature higher than the temperature in production of the normal magnesium carbonate in the first step, without fail.

When the temperature is lower than the temperature in the first step or the temperature of lower than 35° C., the objective tubular basic magnesium carbonate may not be obtained, or it is not practical due to reduced production efficiency resulting from extremely long time reaction time. The temperature higher than 80° C. results in inferior uniformity of the produced basic magnesium carbonate particles, and contamination of amorphous to spherical aggregated particles may be obvious.

Further, also in the second step, stirring of the reaction liquid is preferably carried out for the purpose of keeping the uniformity of the reaction, similarly to the case in first step. The solid content of suspension of the normal magnesium carbonate to be subjected to the heat treatment is not particularly limited, but may be selected according to the amount of the basic magnesium carbonate to be produced, however, desirably, it is preferred that the solid content of the resultant suspension of basic magnesium carbonate is adjusted to be 5 to 100 g/L. When the content is less than 5 g/L, production efficiency may be reduced thereby leading to unpractical result. When the content is greater than 100 g/L, viscosity of the suspension becomes so high that it may be hard to be stirred, thereby impairing the uniformity of the product as well as reducing the production efficiency.

Furthermore, with regard to the pH of the suspension of the normal magnesium carbonate in the heat treatment, it is desirable that the condition of the pH is 7.5 to 11.5, and preferably 8.5 to 11.5. When the pH is lower than 7.5, the production rate of the basic magnesium carbonate from the normal magnesium carbonate is lowered, thereby reducing the production efficiency, and in addition, the normal magnesium carbonate may remain in the final product. Moreover, when the pH is higher than 11.5, uniformity of the particles of the final product may be impaired, and amorphous to spherical particles may be easily mixed.

In order to adjust the pH to fall within the range, ratio of the amount of the water soluble magnesium salt to the water soluble carbonate salt may be regulated, or an acidic substance or an alkaline substance may be added in the second step to achieve the adjustment. In the former case, adjustment to the acidic condition can be achieved by increasing the amount of the water soluble magnesium salt, while adjustment to the alkaline condition can be achieved by increasing the amount of the water soluble carbonate salt. In the latter case, examples of the acidic substance which can be utilized for the addition include such as hydrochloric acid, sulfuric acid and nitric acid, while examples of the alkaline substance which can be utilized for the addition include such as sodium hydroxide, potassium hydroxide and aqueous ammonia.

In the second step, it is desired that heating and stirring is continued until the production of the basic magnesium carbonate is completed. Completion of the production of the basic magnesium carbonate can be determined by measuring the pH, electric conductivity or the like of the suspension. For example, with regard to pH, the pH of the suspension is gradually reduced during the time while the production of the basic magnesium carbonate proceeds while the pH is almost constant after completing the production.

According to the method as described above, the tubular aggregated particles comprising the flaky fine crystal of basic magnesium carbonate can be obtained. When it is desired that a particle shape of the tubular aggregated particles thus produced to be more uniform, in other words, it is desired that one with a relatively low or no ratio of the particles having the shape other than the tubular aggregated particle is produced, the reaction condition in the first step and second step is desirably regulated ad libitum as described below.

With regard to the kind of the water soluble carbonate salt used in the first step, use of a strong alkaline carbonate salt is suitable for the selective production of the tubular aggregated particles, and more desirably, use of sodium carbonate and/or potassium carbonate is preferred.

With regard to the temperature in the production of the columnar particle of the normal magnesium carbonate in the first step, when the temperature is relatively low or relatively high, columnar aggregated particles of the basic magnesium carbonate are tend to be mixed finally. In order to decrease the ratio of the contamination or avoid the contamination, it is preferred that the temperature is adjusted to be appropriate one, and more suitably, it is preferable that the temperature in the production of the columnar particle of the normal magnesium carbonate in the first step is set to be 25 to 55° C., more suitably 28 to 50° C.

Also with regard to the temperature for the heat treatment of the suspension of the columnar particle of the normal magnesium carbonate in the second step, when the temperature is relatively low or relatively high, columnar aggregated particles of the basic magnesium carbonate are tend to be mixed. In order to decrease the ratio of the contamination or avoid the contamination, since there is a suitable temperature range, it is preferred that the temperature is adjusted to be 40 to 70° C., and more desirably 45 to 65° C. With regard; to the pH in the heat treatment of the suspension of the columnar particle of the normal magnesium carbonate in the second step, the tubular aggregated particles can be more selectively produced in higher temperature, and specifically, the pH is set to be 9.5 to 11.5, and preferably 10.0 to 11.5.

With regard to the relationship between the temperature in the production of the columnar particle of the normal magnesium carbonate in the first step and the temperature in the heat treatment of the suspension of the columnar particle of the normal magnesium carbonate in the second step, it was already described that the temperature must be higher in the second step than that in the first step. However, in order to more selectively produce the tubular aggregated particles, it is more preferred that the difference in the temperature between those in the first step and the second step is adjusted appropriately. When the difference in temperature is too small, columnar aggregated particles are apt to be produced, while columnar aggregated particles are tend to be mixed when the difference in the temperature is too great.

Specifically, the tubular aggregated particles can be more selectively obtained when the difference in temperature between those in the first step and the second step is set to be 2 to 35° C., preferably 2 to 25° C., and more preferably 2 to 20° C. With regard to the suitable difference in temperature employed in order to decrease the ratio of the particles other than the tubular aggregated particle or avoid the contamination thereof, it varies depending on the temperature in the production of the columnar particle of the normal magnesium carbonate in the first step, and the pH in the heat treatment of the suspension of columnar particles of the normal magnesium carbonate in the second step.

For example, when the pH in the second step is set to be 10.5, it is preferred for the purpose of producing the tubular aggregated particle in a more selective manner: the difference in temperature is as great as 20 to 35° C. when the temperature in the first step is as low as 25 to 35° C.; the difference in temperature is 5 to 25° C. when the temperature in the first step is 35 to 45° C.; and the difference in temperature be as small as 2 to 15° C. when the temperature in the first step is as high as 45 to 55° C.

Taken together all aspects as described above, suitable conditions for more selective production of the tubular aggregated particles of the basic magnesium carbonate are that: a strong alkaline carbonate salt is used as the water soluble carbonate salt in the first step; the temperature in the production of the normal magnesium carbonate in the first step is set to be 25 to 55° C.; a suspension of the columnar particles of the normal magnesium carbonate is subjected to a heat treatment at a pH of 9.5 to 11.5, and a temperature of 40 to 70° C. in the second step; and the difference in temperature between those in the first step and the second step is set to be 2 to 35° C.

In addition thereto, the tubular aggregated particle can be produced more selectively, also by appropriate selection or regulation of the kind of the water soluble magnesium salt or the water soluble carbonate salt used in the first step, the concentration of the aqueous solution thereof and the ratio of the amount, the diameter of the columnar particle of the normal magnesium carbonate produced in the first step, the holding time for the production of the normal magnesium carbonate in the first step, the the temperature rising rate in the transition from the first step to the second step, and the like.

However, the preferable condition for more selectively producing the tubular aggregated particle as described above may vary depending on various conditions in each of the first step and second step, as well as the combination of various conditions in the first step and the second step, and the like, which may not be determined primarily. In other words, the condition for the heat treatment of the suspension of normal magnesium carbonate in the second step for more selectively producing the basic magnesium carbonate may vary depending on the condition for producing the normal magnesium carbonate and the feature of thus produced normal magnesium carbonate in the first step.

Therefore, in a desired process, various conditions in the first and second step as described above are controlled ad libitum such that the tubular aggregated particles are more selectively produced: the type of the water soluble magnesium salt or the water soluble carbonate salt used in the first step, the concentration of the aqueous solution thereof or the ratio of the amount, the temperature for producing the normal magnesium carbonate in the first step, the holding time for the production of the normal magnesium carbonate, the diameter of the normal magnesium carbonate produced in the first step, the temperature rising rate in the transition from the first step to the second step, the difference in temperature between those in the first step and the second step, and the pH in the heat treatment of the columnar particle of the normal magnesium carbonate in the second step.

As set forth above, the basic magnesium carbonate which is a tubular aggregated particle of flaky fine crystals can be produced according to the first and second step in the S method.

Next, the second method (hereinafter, referred to as G method) is explained.

The G method comprises a first step for preparing a solution of magnesium hydrogen carbonate by introducing a gas containing carbon dioxide into a suspension of magnesium hydroxide, a second step for producing a columnar particle of normal magnesium carbonate by adjusting the solution of a magnesium hydrogen carbonate to have the pH of 7.5 to 11.0, and a third step for producing a basic magnesium carbonate by adjusting a suspension of columnar particles of the normal magnesium carbonate to be the pH of 9.0 to 12.0, and the temperature of 30 to 75° C., followed by keeping the temperature of within the range described above. By providing these three steps, a basic magnesium carbonate comprising a tubular aggregated particle of flaky fine crystals can be produced.

The first step is a step for preparing a solution of magnesium hydrogen carbonate by introducing a gas containing carbon dioxide into a suspension of magnesium hydroxide, and the magnesium hydroxide which is a material used herein is not particularly limited, but any one of various types can be utilized in addition to magnesium hydroxide produced by a so called seawater method in which calcium hydroxide is added to ocean water to precipitate magnesium hydroxide.

For example, a naturally yielded magnesium hydroxide ore (brucite) which is ground as it stands, a naturally yielded magnesium carbonate ore (magnesite) or a hydrate of magnesium oxide which is produced by burning of a magnesium hydroxide ore, or the like can be used. Additionally, a suspension of magnesium hydroxide may be also used which is obtained by adding an alkaline substance such as sodium hydroxide or calcium hydroxide to an aqueous solution of a water soluble magnesium salt such as magnesium sulfate or magnesium chloride to precipitate magnesium hydroxide.

With regard to the particle size of magnesium hydroxide, more finely divided particle is preferred on behalf of the excellent reactivity with the carbon dioxide gas and reducing the time required for the first step. Accordingly, those having a mean particle diameter of 50 μm or less are preferable, and those having a mean particle diameter of 25 μm or less is more preferable. Furthermore, with regard to the concentration of the suspension of magnesium hydroxide, it may be adjusted ad libitum taking into account of the amount of basic magnesium carbonate to be produced finally. However, that too low concentration results in inferior production efficiency, and to the contrary, by too high concentration, the viscosity of the suspension increases and may inhibit a uniform reaction. Therefore, it is preferable that the concentration is 5 g/L to 200 g/L, desirably 10 g/L to 100 g/L, and more desirably 10 to 50 g/L.

Also, the gas containing carbon dioxide for use in the first step is not particularly limited. Therefore, carbon dioxide supplied from a steel cylinder or the like, diluted gas thereof with air or the like, or a gas containing carbon dioxide such as an exhaust combustion gas can be utilized. Concentration of carbon dioxide included in the gas containing carbon dioxide is not also particularly limited, however, too low concentration may result in inferior efficiency to produce magnesium hydrogen carbonate. Therefore, it is suitable that a gas containing 5% by volume or greater carbon dioxide is used.

Also with regard to the method for the introduction of a gas containing carbon dioxide, any one of various gas-liquid mixing apparatuses can be applied. For example, a method in which a gas containing carbon dioxide is bubbled through a gas introducing tube, or a method in which a gas containing carbon dioxide is introduced using a bubble tower into a suspension of magnesium hydroxide, and the like may be included. When the gas containing carbon dioxide is introduced, it is preferable that the gas is finely dispersed permitted to promote the contact of the gas and liquid for the purpose of an efficient reaction of carbon dioxide with magnesium hydroxide. For example, the gas can be finely dispersed by stirring the suspension of magnesium hydroxide and the reaction efficiency of magnesium hydroxide with carbon dioxide can be increased.

In the first step, it is preferred that 90% or more, and desirably total amount of the magnesium hydroxide used as a raw material is converted into magnesium hydrogen carbonate, because when the amount of magnesium hydroxide which is not converted into magnesium hydrogen carbonate is much, a uniform reaction is inhibited in the following second step and third step, which may lead to inferior uniformity of the particle shape of the tubular aggregated particles of the basic magnesium carbonate which is the final product.

With regard to the conversion from magnesium hydroxide to magnesium hydrogen carbonate, it can be determined by measuring the pH, electric conductivity or the like of the liquid. For example, in with regard to the pH of the liquid, a pH of the suspension of magnesium hydroxide prior to introducing the gas containing carbon dioxide is approximately 9 to 11, while in case when the total amount of the magnesium hydroxide is converted into magnesium hydrogen carbonate, a pH of the liquid becomes an approximately neutral pH. In the first step, it is preferable that a gas containing carbon dioxide is introduced until the pH of the liquid becomes 8.0 or lower, and it is more preferable that the gas is introduced until the pH of the liquid becomes 7.5 or lower.

Liquid temperature in the introduction of the gas containing carbon dioxide into the suspension of magnesium hydroxide is not also particularly limited, however, when liquid temperature is too high, the solubility of magnesium hydrogen carbonate is reduced. Consequently, not only the amount of unreacted magnesium hydroxide which remains in thus prepared magnesium hydrogen carbonate solution is increased, but also decomposition of magnesium hydrogen carbonate prior to the completion of the reaction in the first step is found. Accordingly, when a gas containing carbon dioxide is introduced into a suspension of magnesium hydroxide, the liquid temperature is preferably kept at 35° C. or lower, and more preferably 30° C. or lower.

In addition, it is preferable that undissolved residues such as unreacted magnesium hydroxide and other impurity are eliminated after the introduction of a gas containing carbon dioxide into a suspension of magnesium hydroxide. Accordingly, a solution of magnesium hydrogen carbonate with less impurity can be prepared, and therefore, a basic magnesium carbonate of high purity and uniformity of particles can be obtained in the following third step.

As described above, a solution of magnesium hydrogen carbonate is prepared in the first step.

In subsequent second step, pH of the solution of magnesium hydrogen carbonate prepared in the first step is adjusted be 7.5 to 11.0 to produce a columnar particle of a normal magnesium carbonate. Also in this second step, stirring of the reaction liquid is preferably carried out for the purpose of keeping uniformity of the reaction, similarly to the case in the first step. The normal magnesium carbonate referred to herein is represented by the chemical formula of $MgCO_3 \cdot nH_2O$, wherein n is 3 in general as for the value of n. However, any one in which n is other than 3 is also permitted without limitation as long as it follows the production condition or has the shape as described below.

With regard to the concentration of the solution of magnesium hydrogen carbonate subjected to the second step is not particularly limited, but the solution prepared in the first step may be used as it stands, or diluted or concentrated solution taking into account of the amount of the normal magnesium carbonate to be produced in the second step may be also used. However, too low concentration of the solution of magnesium hydrogen carbonate results in inferior production efficiency, and to the contrary, by too high concentration, the viscosity of the suspension of columnar particles of the normal magnesium carbonate to be produced is increased and the progress of the uniform reaction may be inhibited. Therefore, desirably, it is preferred that the concentration of the solution of magnesium hydrogen carbonate is adjusted such that the solid content in the suspension of columnar particles of the normal magnesium carbonate produced in the second step becomes 10 to 300 g/L.

In the second step, it is required that the pH entered into the neutral region in the first step is adjusted to be alkaline state, and for the purpose, an appropriate amount of an alkaline substance is added to the solution of magnesium hydrogen carbonate prepared in the first step to adjust the pH. Further, after the adjustment, the pH must be within the range of 7.5 to 11.0. The alkaline substance used herein is not particularly limited, but sodium hydroxide, potassium hydroxide, aqueous ammonia or the like may be used.

In the second step, the pH must be adjusted as described above, since in cage when the pH is lower than 7.5, the tubular aggregated particle of the basic magnesium carbonate cannot be obtained in the following third step. To the contrary, when the pH is higher than 11.0, the normal magnesium carbonate becomes unstable, which leads to the production of the basic magnesium carbonate prior to completion of the production of the normal magnesium carbonate, or to direct production of the basic magnesium carbonate from magnesium hydrogen carbonate. Thus, uniformity of the particles of the basic magnesium carbonate as a final product may be significantly impaired, and the required amount of the alkaline substance used for adjusting the pH is increased, which is not economically good.

For producing the columnar particle of the normal magnesium carbonate in the second step, it is preferable that after adjusting the pH of the solution of magnesium hydrogen carbonate prepared in the first step to be 7.5 to 11.0, the reaction proceed until completion of the production of the normal magnesium carbonate. With regard to the completion of the production of the normal magnesium carbonate, it can be confirmed by measuring the pH, electric conductivity or the like of the liquid to observe stabilization of the value.

Furthermore, the temperature then is desirably 20 to 55° C., and more desirably 30 to 55° C. When the temperature is lower than 20° C., amorphous aggregated particles are apt to be mixed in addition to the tubular aggregated particles of the basic magnesium carbonate in the following third step. Also when the temperature is higher than 55° C., to the contrary, uniformity of the particles is apt to be impaired in the third step.

In the second step, the pH is adjusted as described above, and desirably the temperature is also regulated as described above to proceed until completion of the production of the normal magnesium carbonate, thereby allowing the production of the columnar particle of the normal magnesium carbonate. It is desired that, with regard to the shape of the columnar particle, preferable shape is a diameter of 0.5 to 10 μm and a length of 5 to 500 μm. In particular, when the diameter of the columnar particle is less than 0.5 μm or greater than 10 μm, the tubular aggregated particle of the basic magnesium carbonate intended by the present invention may not be obtained in the following third step.

It is desired that the shape of the columnar particle of the normal magnesium carbonate produced in the second step is regulated depending on the shape of the tubular aggregated particle of the basic magnesium carbonate to be produced in the following third step. In other words, the tubular aggregated particle of the basic magnesium carbonate produced in the present invention is speculated that a unique particle shape of tubular is formed by the precipitation of flaky fine crystals of a basic magnesium carbonate on the surface of the columnar particle of the normal magnesium carbonate produced in the second step.

Moreover, the shape of the tubular aggregated particle of the basic magnesium carbonate produced in the third step, particularly the diameter and length is affected by the diameter and length of the columnar particle of the normal magnesium carbonate produced in the second step, and thus, it is desired that the diameter and length of the normal magnesium carbonate produced in the second step is regulated depending on the shape of the tubular aggregated particle of the basic magnesium carbonate which is the object of the production. For regulating the diameter and length of the normal magnesium carbonate, the pH and temperature in the production of the normal magnesium carbonate in the second step may be controlled appropriately.

For example, with regard to the pH in the second step, the columnar particle of the normal magnesium carbonate having a smaller diameter can be obtained at the higher pH within the aforementioned range while the columnar particle of the normal magnesium carbonate having a greater diameter can be obtained at the lower pH. Moreover, with regard to the temperature in the second step, the columnar particle of the normal magnesium carbonate having a smaller diameter can be obtained at the higher temperature within the aforementioned range while the columnar particle of the normal magnesium carbonate having a greater diameter can be obtained at the lower temperature.

For examples, in cases where the temperature for producing the normal magnesium carbonate in the second step is 45° C.: when the pH is set to be 8.0, the columnar particle of the normal magnesium carbonate of a diameter of 5 to 10 μm and a length of 20 to 150 μm; when the pH is 9.0, the diameter is 1 to 5 μm and the length is 20 to 100 μm; and when the pH is 10.0, the diameter is 0.5 to 2 μm and the length is 10 to 80 μm.

Additionally, thus produced columnar particle of the normal magnesium carbonate may be filtrated and washed once, thereby capable of eliminating the alkaline substance added in the second step, which is desired in light of possible reduction of impurities included in the product. Accordingly, the columnar particle of a normal magnesium carbonate is produced from the solution of magnesium hydrogen carbonate in the second step.

In the third step, which is the final step subsequent to the second step, a basic magnesium carbonate is produced under a condition at pH of 9.0 to 12.0 and temperature of 30 to 75° C. from the suspension of the columnar particle of the normal magnesium carbonate obtained in the second step. Furthermore, also in the third step, stirring of the reaction liquid is preferably carried out for the purpose of keeping uniformity of the reaction, similarly to the cases in the first step and second step.

The solid content of the suspension of columnar particles of the normal magnesium carbonate to be subjected to the third step is not particularly limited. Therefore, the suspension obtained in the second step may be directly used, or may be diluted or concentrated ad libitum according to the amount of the basic magnesium carbonate to be produced. However, desirably, it is preferred that the solid content of the suspension of the basic magnesium carbonate obtained in the third step is adjusted to be 5 to 100 g/L. When the solid content is less than 5 g/L, production efficiency may be reduced thereby leading to unpractical result. When the content is greater than 100 g/L, viscosity of the suspension becomes so high that stirring may be insufficient, thereby impairing the uniformity of the product as well as reducing the production efficiency.

It is necessary and important that the temperature in the production of basic magnesium carbonate in the third step is 30 to 75° C. When the temperature is lower than 30° C., the objective tubular basic magnesium carbonate may not be obtained, or it is not practical due to reduced production efficiency resulting from extremely long time for the reaction. When the temperature is higher than 75° C., uniformity of the produced basic magnesium carbonate particle may be impaired, and contamination by amorphous to spherical particles becomes prominent.

It is required that the pH in the step is set to be 9.0 to 12.0, since when the pH is less than 9.0, the production rate of the basic magnesium carbonate from the normal magnesium carbonate is decreased, thereby reducing the production efficiency, and additionally, the normal magnesium carbonate may remain in the final product. Moreover, when the pH is higher than 12.0, uniformity of the particles of the final product may be impaired, and thus, amorphous to spherical particles may be easily mixed.

Moreover, it is desired that the pH in the third step is set to be higher than the pH in the production of the columnar particle of the normal magnesium carbonate in the second step, and more desirably, the pH is preferably 0.3 or higher. Accordingly, more efficient production of the tubular aggregated particle of the basic magnesium carbonate having superior uniformity and a variety of excellent powder properties is enabled. In order to adjust the pH to fall within this range, an acidic substance or an alkaline substance may be added in the third step. Examples of the available acidic substance which may be added include hydrochloric acid, sulfuric acid, nitric acid, acetic acid and the like, while examples of the available alkaline substance which may be added include sodium hydroxide, potassium hydroxide, aqueous ammonia and the like.

The temperature and pH in the third step is desirably adjusted depending on the shape of the normal magnesium carbonate produced in the second step, particularly on the diameter and the length. Accordingly, tubular aggregated particles of the basic magnesium carbonate having a more uniform shape can be obtained. Specifically, when the diameter of the normal magnesium carbonate is short, the pH and temperature in the third step is preferably lower, and to the contrary, when the diameter of the normal magnesium carbonate is long, the pH and temperature in the third step is preferably higher.

In the third step, it is desired that stirring is continued while keeping the temperature within the aforementioned range, until the production of the basic magnesium carbonate is completed. For a reference, it is not necessary then to continuously keep the temperature of immediately after a temperature adjusted to be of 30 to 75° C., but the temperature may vary within the above range of the temperature. However, the variation is preferably as small as possible. Completion of the production of the basic magnesium carbonate can be determined by measuring the pH, electric conductivity or the like of the suspension. For example, with regard to pH, the pH of the suspension is going to be lower during the time while the production of the basic magnesium carbonate proceeds, and to the contrary, after completion of the production, the pH is almost constant.

As described above, it is important to appropriately control the reaction conditions of respective steps in the G method, and no problem is involved in combining the aforementioned suitable conditions, preferable conditions, and more preferable conditions and the like ad libitum. For example, no problem is involved in combining more preferable conditions and suitable conditions.

The following are the desirable examples of combinations of those conditions for producing the tubular aggregated particle of the basic magnesium carbonate in a more efficient manner: magnesium hydroxide having a mean particle diameter of 50 μm or less is used, and a gas containing carbon dioxide is introduced until the pH becomes 8.0 or lower while keeping the concentration of the suspension of 10 to 100 g/L, and the liquid temperature of 35° C. or lower in the first step; the pH is adjusted to alkaline within the range of 8.0 or higher and 11.0 or lower, and the temperature is set to be 20 to 55° C. to allow the production of the columnar particle of a normal magnesium carbonate having a diameter of 0.5 to 10 μm and a length of 5 to 500 μm in the second step; and after adjusting the pH to fall within the range of 9.0 to 12.0 and to be higher pH than that in the second step, and the temperature to be 30 to 75° C., the production of a basic magnesium carbonate is allowed by keeping the aforementioned range of the temperature in the third step.

Furthermore, in preferable conditions of the production in the first step: magnesium hydroxide having a mean particle diameter of 25 μm or less is used, and a gas containing carbon dioxide is introduced until the pH becomes 7.5 or lower while keeping the concentration of the suspension of 10 to 50 g/L, and the liquid temperature of 30° C. or lower, followed by elimination of insoluble impurities; in the second step, the pH is adjusted to alkaline within the range of 7.5 or higher and 11.0 or lower, and the temperature is set to be 30 to 55° C. to allow the production of the columnar particle of a normal magnesium carbonate having a diameter of 0.5 to 10 μm and a length of 5 to 500 μm, followed by filtration and washing to eliminate the alkaline substance added in the second step; and in the third step, after adjusting the pH to fall within the range of 9.0 to 12.0 and to be higher pH than that in the second step by 0.3 or higher, and the temperature to be 30 to 75° C., production of a basic magnesium carbonate is allowed by keeping the aforementioned range of the temperature, and thus, it is possible to obtain the tubular aggregated particle of a basic magnesium carbonate having superior uniformity of the particles and a variety of excellent powder properties in a stable manner.

As described in above, a basic magnesium carbonate comprising a tubular aggregated particle of flaky fine crystals can be produced by the first, second and third steps in the G method.

For a reference, according to the G method, it is advantageous in the reduction of impurities included in the product, or in facilitating the wash of impurities, in comparison with the S method. More specifically, an anionic component of the water soluble magnesium salt and a cationic component of the water soluble carbonate salt used in the first step are included in the product according to the S method, however, these components are not included according to the G method. Therefore, the G method may be referred to as a more preferable method in cases where a basic magnesium carbonate having a higher purity is intended to obtain, or in cases where a wash of impurities is intended to be facilated.

Thus, the basic magnesium carbonate produced according to the S method or G method can be utilized in the state of a suspension, or in the state of dried powder after dehydration or drying, depending on the use thereof. When it is utilized in the state of a suspension, the suspension following the reaction may be used directly, or may be diluted or concentrated ad libitum depending on the use thereof. When it is utilized in the form of dried powder, the dried powder may be obtained after a dehydration step or drying step.

However, aggregation in drying may occur in the drying process, and thus crushing may be required in the following step. In some cases, crushing may lead to the phenomenon of disruption of the particle shape, therefore, more preferable procedure for obtaining the dried powder may be a method in which a step for substituting the solvent of the suspension of the basic magnesium carbonate post production with an organic solvent such as alcohol, or for washing with an organic solvent such as alcohol after dehydration is provided, followed by drying.

Dried powder in which aggregation is suppressed by drying is suppressed is obtained by performing the substitution of the solvent with an organic solvent such as alcohol or the wash with alcohol or the like. As the organic solvent herein used, one having low solubility of the basic magnesium carbonate is suitable, and examples which may be used include such as methyl alcohol, ethyl alcohol and acetone.

Alternatively, even if the substitution of the solvent with an organic solvent or the wash as described above is not performed, a drying method accompanied by less aggregation upon drying may be adopted. Dried powder in which suppressed aggregation by drying is suppressed can be obtained through using, such as spray dryer or fluidized bed dryer, vacuum dryer, vacuum lyophilizer and agitation dryer. There is no problem in utilization of thus resulting basic magnesium carbonate in each field following a treatment with an organic surface treatment agent such as a fatty acid salt, a resinate, or any one of various surfactants including coupling agents, or an inorganic surface treatment agent such as phosphate or sulfate.

The basic magnesium carbonate of the present invention described hereinabove exhibits a novel shape that is a tubular aggregated particle of flaky fine crystals, and on behalf of the unique shape that is tubular, it can have a variety of excellent characteristics such as high specific surface area, high oil absorbing property, high water absorbing property, low bulk density and porosity. Taking advantages of such a unique shape and excellent characteristics, the basic magnesium carbonate of the present invention can be utilized in a variety of fields.

At first, a filler for low density paper and low density paper in which the tubular aggregated particles of the basic magnesium carbonate according to the present invention is utilized is described. The filler for low density paper of the present invention is characterized by including the tubular aggregated particles of flaky fine crystals of a basic magnesium carbonate, and the low density paper of the present invention is characterized by containing the tubular aggregated particles of flaky fine crystals of a basic magnesium carbonate as a filler. In addition to the characteristic of low density, a feature of high rigidity can be obtained.

The tubular aggregated particle of a basic magnesium carbonate used as a filler for low density paper is not particularly limited as long as it has a shape as described hereinabove. However, too large external diameter or too great length may result in reduction of a tensile strength or a tearing strength, although no problem is involved in changes into the low density. To the contrary, when those values are too small, exerting the effect of changes into the low density may be difficult.

Taking into consideration of these aspects, with regard to the size of the tubular aggregated particle of a basic magnesium carbonate, the external diameter of 1 to 20 µm, the length of 5 to 200 µm, and the ratio of length/external diameter of 2 to 20 are suitable. Furthermore, with regard to the internal diameter, when the internal diameter is closer to the value of the external diameter, voids are increased, which leads to the greater effect toward changes into the low density, however, when the wall portion of the tubular aggregated particle is too thin, a part of the particles may be broken when it is stressed in the step of papermaking, thereby reducing the effect. Taking into account of these aspects, it is suitable that the tubular aggregated particles having an external diameter of 1 to 20 µm, an internal diameter of 0.5 to 5 µm, a ratio of internal diameter/external diameter of 0.2 to 0.9 and a length of 5 to 200 µm are prepared.

A filler including the tubular aggregated particles of a basic magnesium carbonate is the filler for low density paper of the present invention, and paper containing this as a filler is the low density paper of the present invention. Content of the same is not particularly limited, and may be regulated ad libitum depending on the quality of the objective paper. For a reference, the greater content of the tubular aggregated particle of a basic magnesium carbonate results in achieving the greater effect on changes into the low density of the paper, and thus the paper having higher rigidity can be obtained.

However, if the content is too small, effect of changes to the low density becomes less, and to the contrary, if the content is too great, the strength property such as a tensile strength and a tearing strength, or operativity in the papermaking step is reduced, although paper that is excellent in terms of the density and rigidity may be provided. Therefore, when a balance among the density or rigidity of the paper, other quality, and operativity and the like is considered, the preferable condition is that content of the tubular aggregated particle of the basic magnesium carbonate is set to be 2 to 25% by weight, and desirably 4 to 20% by weight in absolute dry weight of the paper to be produced.

In the filler for low density paper of the present invention, the tubular aggregated particle of a basic magnesium carbonate must be inevitably included, however, in addition thereto, ingredients such as calcium carbonate or kaolin, titanium oxide, silica and talc which are generally blended in a filler may be admixed, if necessary. In particular, when an optical characteristic such as high whiteness or opacity is required as a quality expected for the objective paper, paper accompanied by both characteristics of low density as well as high rigidity which is the effect of the tubular aggregated particle of the basic magnesium carbonate, and a high optical characteristic derived from titanium oxide or calcium carbonate can be obtained by admixing an appropriate amount of titanium oxide or calcium carbonate.

Also, the pulp for use in the low density paper of the present invention may be used without particularly limited, which may be one or a mixed pulp of two or more kinds selected from generally used pulp such as craft pulp made from timber of broadleaf tree or needle-leaved tree as a raw material, chemical pulp such as sulfite pulp or soda pulp, semichemical pulp such as semichemical pulp or chemimechanical pulp, mechanical pulp such as ground wood pulp or thermo mechanical pulp, nontimber fiber pulp made from a raw material such as paper mulberry (*Broussonetia*), mitsumata plant (*Edgeworthia papyrifera*), flax plant (*Linum usitatissimum* L.), hemp (Cannabis sativa) or kanaf, deinked pulp made from recycled waste paper as a raw material.

Low density paper suited for use and production of the filler for low density paper is not particularly limited in connection with the grade, use or the like thereof, but any one of various types can be applied. Illustrative examples of the various paper include uncoated paper for printing such as high class to low class paper for printing or thin paper for printing, base paper of coated paper for printing such as art paper or coat paper, base paper of finely coated paper for printing, communication paper such as paper for PPC or paper for recording information, paper for news paper, base paper for wall paper and the like.

Weighing of the paper and content of the filler in the paper to be produced is not also particularly limited as long as they fall within the range to achieve predetermined changes into the low density and rigidity, but may be selected depending on the grade or use of the paper as described above. Preferably, the weighing is 25 to 75 g/m$^2$, and the filler is included in an amount of 5 to 25% by weight per absolute dry weight of the paper. It is desired that 20 to 100% by weight, and more preferably 50 to 100% by weight of the tubular aggregated particle of a basic magnesium carbonate is included in the filler. In addition, needless to say, the filler for low density paper and low density paper of the present invention must contain the tubular aggregated particle of the basic magnesium carbonate inevitably.

The content of the filler referred to herein indicates total content of other filler such as calcium carbonate, kaolin, talc, silica and talc which may be used in addition to the tubular aggregated particle of the basic magnesium carbonate. By setting the weighing and content of the filler as described above, in the low density paper of the present invention, the effects of changes into the low density and improvement of the rigidity is more efficiently exhibited, accompanied by achieving the paper with well balanced strength property such as a tensile strength and a tearing strength, and other quality, for example, optical characteristics such as whiteness and opacity.

The low density paper of the present invention is produced by a conventional papermaking method, for example, by subjecting a slurry for paper including the filler for low density paper of the present invention and various agents for papermaking added into a slurry of the pulp as described above to papermaking. The aforementioned filler contains at least the tubular aggregated particle of flaky fine crystals of a basic magnesium carbonate.

With regard to the agents for papermaking added into the pulp slurry together with the filler described above, agents used in the conventional papermaking such as sizing agent, sizing fixing agent, yield ratio improving agent, water-repellent improving agent, paper strength enhancing agent, water resistance imparting agent, water-repellent agent, anti-foaming agent, slime controlling agent, dye and the like may be also used ad libitum with no problem. Additionally, a water soluble polymer such as starch or water soluble cellulose may be applied to the surface after the papermaking, if necessary. Furthermore, on the surface of the base paper obtained according to the method as described above may be coated by a coating agent containing an inorganic or organic pigment for coating and a binder as active ingredients.

According to thus produced paper containing the tubular aggregated particle of flaky fine crystals of a basic magnesium carbonate as a filler, the density can be reduced in comparison with the paper internally filled with only a generally employed filler such as calcium carbonate, kaolin, titanium oxide, silica and talc. Additionally, rigidity of the paper may be also improved, therefore, the problem of deterioration of rigidity upon saving of paper weight can be solved.

Moreover, since the tubular aggregated particle of flaky fine crystals of the basic magnesium carbonate is a material which is excellent in oil absorbing property as well as water absorbing property, the low density paper of the present invention containing the basic magnesium carbonate is also excellent in quality such as ink receptivity, opacity post printing and printability. Furthermore, the basic magnesium carbonate can be also used as a coating pigment for papermaking, and the coated paper on which the basic magnesium carbonate is coated not only exhibits saving weight but also exhibits excellent ink receptivity and post printing opacity, printability and the like.

Next, it is described that the hollow carrier and functional particle in which the tubular aggregated particle of a basic magnesium carbonate of the present invention is utilized is explained. The hollow carrier of the present invention is a carrier having a novel shape including the tubular aggregated particle of the flaky fine crystals of a basic magnesium carbonate, and the hollow carrier internally including an effective substance is the functional particle of the present invention. The functional particle internally includes various effective substances within the hollow carrier comprising the tubular aggregated particle of the flaky fine crystals of a basic magnesium carbonate, and has excellent characteristics such as sustained release effect, release-controlling property, prevention of degeneration or protection in quality of the encapsulated substance and masking effect.

The functional particle of the present invention is a functional particle having the aforementioned features and having the tubular structure of a hollow carrier comprising a basic magnesium carbonate of which interior includes internally an effective substance such as an aromatic substance, a nutritional supplement, a food additive, medicament, pesticide or fertilizer. Because the functional particle internally includes an active ingredient within the tubular structure of the hollow carrier, it exhibits excellent characteristics such as sustained release property which is a property of gradual release of the encapsulated substance; release-controlling property, i.e., a property of release of the encapsulated substance under a specific condition; prevention or protection of degeneration in quality of the encapsulated substance and masking effect.

For example, when the sustained release property is utilized, it can be a material which keeps an active ingredient releasing for a long time by the internal inclusion of a substance which is readily evaporated or sublimated in ordinary circumstances. For the utilization of the release-controlling property, it can be a material which releases the encapsulated substance under a condition in which the basic magnesium carbonate is decomposed or the tubular structure is disrupted, such as an acidic condition or pressurized condition. Furthermore, by internally including a substance or the like which is easily decomposed in ordinary circumstances through the contact with air and the like, contact with the outside environment is suppressed, and thus, a material with suppressed decomposition of the active ingredient can be also prepared.

Also, by covering the surface with an organic polymer when needed, the masking effect or sustained release effect of the encapsulated substance can be even more improved. The organic polymer used then may be selected ad libitum depending on the use or performance expected, however, when a water soluble polymer which enables use of a water based solvent is used, covering can be comparatively easily executed. Examples of the water soluble polymer which can be used include natural polymers, modified products of a natural occurring polymers and synthetic polymers. Examples of the natural polymers which can be used include starchy substances, mannan, seaweeds, plant viscous substances, microorganism viscous substances, proteins and the like.

More specifically, examples of the starchy substance include sugar cane starch, potato starch, tapioca starch, wheat starch, corn starch and the like; examples of the mannan include alimentary yam paste; examples of the seaweed include glue plant, agar (galactan), sodium alginate and the like; examples of the plant viscous substance include *Hibiscus manihot* L. (*Abelmoschus manihot*), gum tragacanth, gum arabic and the like; examples of the microorganism viscous substance include dextran, levan and the like; and examples of the protein include gelatin, casein, collagen, hide glue and the like.

Examples of the modified product of a natural polymer which may be used include viscose, methyl cellulose (MC), ethyl cellulose (EC), hydroxyethyl cellulose (HEC), carboxymethyl cellulose (CMC) and the like which are cellulose based, soluble starch, carboxymethyl starch (CMS), dialdehyde starch and the like which are starch based, and the like. Examples of the synthetic polymer include polyvinyl alcohol (PVA), sodium polyacrylate, polyethylene oxide and the like.

Among these water soluble polymers, edible biopolymers such as gelatin, casein, myosin, collagen, alginic acid, chitosan, zein, mannan, carrageenan, soybean protein, dextrin, starch, curdlan, xanthan gum and the like are suitable for use as medicinal products and foods.

Moreover, in addition to the effects of active ingredients encapsulated, by utilizing the characteristics of the tubular aggregated particle of the basic magnesium carbonate itself used as a hollow carrier, such as the neutralizing capability of an acidic substance or high adsorption performance derived from porosity in combination, use as a multi functional composite material is enabled.

Examples of the substance encapsulated substance within the hollow carrier include aromatic substances, nutritional agents, food additives, medicaments, pesticides, fertilizers and the like. Examples of the aromatic substance include flavor of coffee, tea, fruit, vanilla, skipjack, shrimp, crab and the like, hinokitiol and the like. Use of the hollow carrier of the present invention can result in improvement of the storage stability thereof through preventing the oxidation or moisture absorption, in addition to maintenance for a long period of time of the flavor or the flavor strength. Examples of the nutritional agent include vitamins such as vitamin C and E, additives for health foods such as gymnema, heme iron and the like. Similarly, stabilization against the heat, light and oxidation, as well as a masking effect for the taste such as bitterness or sourness can be achieved.

Regarding medicament, by encapsulating any one of various medical ingredients, formulations having a function such as sustained release property, release-controlling property, protection property and masking property can be prepared. Examples of the encapsulated medicament include medicaments affecting nerve and sensory organs, medicaments affecting circulation organs, medicaments affecting respiratory organs, medicaments affecting digestive organs, hormone drugs, medicaments affecting urogenital and anal organs, dermatologic preparations, medicaments for dental and oral use, drugs affecting metabolism, medicaments affecting tissue and cellular functions, medicaments against pathogenic organisms, and the like.

Specifically, examples of the medicament affecting nerve and sensory organs include: drugs affecting central nervous system such as general anesthetics, hypnotic sedatives, anti-anxiety agents, anti-epileptics, anti-pyretic analgesic anti-flash agents, analeptics, stimulants, anti-parkinsonian agents, agents for psychoneuron, and combination cold remedy; drugs affecting peripheral nervous system such as local anesthetics, skeletal muscle relaxants, autonomics, anti-spasmodics, diaphoretics and anhidrotics; drugs affecting sensory organs such as agents for ophthalmic use, agents for otological use, anti-motion sickness agents and the like.

Examples of the medicament affecting circulation organs include cardiotonics, anti-arrhythmic agents, diuretic agent, hypotensive agent, capillary stabilizers, vasoconstrictors, vasodilators, agents for hyperlipidemia and the like. Examples of the drug affecting respiratory organs include respiratory stimulants, anti-tussive agent, expectorants, anti-tussive expectorants, bronchodilators, gargling agents and the like. Examples of the drug affecting digestive organs include stegnotics, intestinal regulators, agents for peptic ulcer, stomachics and digestive agents, antacids, purgatives, clysters, cholagogues, combination gastrointestinal agents and the like.

Examples of the hormone formulation include pituitary hormone preparations, salivary gland hormone preparations, thyroid•parathyroid hormone preparations, protein assimilation steroid agents, adrenal hormone preparations, androgenic hormone preparations, estrogen, progesterone preparations, mixed hormone preparations, anti-hormonal agents and the like.

Examples of the drug affecting uro-genital and anal organs include agents affecting urinary organs, agents affecting genital organs, venereal disease protecting agents, uterotonic agents, contraceptives, anti-hemorrhoidals and the like. Examples of dermatologic preparations include sterlizing agents for dermatologic use, wound protective agents, agents for purulence, analgesic•anti-itching•astringent•anti-inflammatory agents, agents for parasitics, medicated emollients, caustics, hair remedies, hair growth stimulating agent, hair removing agents, hair coloring agents, hair tonics, medicated bath preparations and the like. Examples of the drug for dental and oral use include topical anesthetic agents for dental use, dental pulp devitalizing agents, analgesic sedative agents for dental use, disinfectant agents for root canal and carious cavity, dental pulp mummifying agents, root canal filling agents, dental pulp covering agents, antibiotic preparations for dental use and the like.

Examples of the drug affecting metabolism include: various vitamin pills such as vitamin A, vitamin D preparations, vitamin $B_1$ preparations, vitamin B preparations, vitamin C preparations, vitamin E preparations, vitamin K preparations and mixed vitamin preparations; analeptics such as calcium supplements, mineral formulations, saccharide agents, organic acid formulations, protein amino acid formulations, organotherapeutics and agents for infants; drugs affecting blood•body fluid such as blood substitutes, hemostatics, anti-coagulants; drugs for artificial dialysis such as agents for artificial kidney dialysis and agents for peritoneal dialysis; agents for hepatic diseases, antidotes, agents for habitual intoxication, therapeutic agents for gout, enzyme preparations, agents for diabetes mellitus, combined formulations affecting metabolism and the like.

Examples of the medicinal products affecting tissue and cellular functions include cellular function activating drugs such as chlorophyll preparations and dye preparations, tumor suppressing agents such as alkylating agents, antimetabolites, tumor suppressing antibiotic preparations and tumor suppressing plant ingredient preparations, radioactive medicaments, antiallergic agents such as anti-histamic agents, agents for irritation therapy and nonspecific immunogen preparations and the like.

Examples of the medicaments against pathogenic organisms include antibiotic preparations such as those which act on a Gram positive bacterium, those which act on a Gram negative bacterium, those which act on a Gram positive-negative bacterium, those which act on a Gram positive bacterium and mycoplasma, those which act on a Gram positive-negative bacterium, *Rickettsia* and *Chlamydia*, those which act on an acid fast bacterium and those which act on a mold, chemotherapeutic agents such as sulfa preparations, antituberculous agents, antileprosy agents, synthetic antibacterial agents and antiviral agents, biological preparations such as vaccines, toxins and toxoids, antitoxins and leptospire sera, blood preparations, formulations for use in a biological test and mixed biological preparations, and drugs against parasites such as antiprotozoan agents and insecticide and the like.

More specifically, when medicament which stimulates on visceral mucosa in digestive organs and the like or which exerts a strong side effect such as aspirin or penicillin is encapsulated, these medical ingredients are gradually released from the end of the tubular aggregated particle of the hollow carrier. Thus, stimulus or side effect can be alleviated, and maintenance of the drug efficacy can be executed for a long time.

Furthermore, by internally including a medical ingredient or a useful microorganism which is comparatively susceptible to an acid, these ingredients or microorganisms can be protected from gastric acid. Therefore, the more of these ingredients or microorganisms can be permitted to act effectively on a target affected part to which the therapy is intended. Moreover, when a digestive, a digestive enzyme agent or the like is encapsulated, a formulation having a release-controlling property may be also prepared which releases these ingredients after decomposition of the basic magnesium carbonate, which is a hollow carrier, by gastric acid.

Examples of the pesticide include various insecticides, repellents of insects, germicides and fungicides, herbicides, rodenticides, plant growth regulators and the like; examples of the fertilizer include nitrogen based fertilizers such as ammonium sulfate, ammonium chloride, ammonium nitrate, sodium nitrate and lime nitrate and urea, phosphoric acid based fertilizers such as superphosphate of lime, multiple superphosphate of lime and water soluble phosphoric acid, potash based fertilizers such as sulfate of potash, chloride of potash, sulfate of potash magnesia and soluble potash, as well as fertilizers containing a pesticide, pyroligneous acid and the like.

The functional particle as described above can be produced by internally including a desired substance, for example, an effective substance such as an aromatic substance, a nutritional agent, a food additive, a medicament, pesticide or fertilizer within the basic magnesium carbonate comprising a tubular aggregated particle of flaky fine crystals. Method of allowing the internal inclusion is not particularly limited, however, the following method can be widely applied, and is comparatively convenient and suitable.

First, one or more desired active ingredient substances are dissolved or suspended in a solvent. In instances of the state of a suspension, since the particle in the solution must be smaller than the internal diameter of the hollow carrier which is subsequently charged, sufficient dispersion is particularly required in case of solid particles using an ultrasonic dispersion machine and the like. Furthermore, higher concentration is suited because the amount of the substance which can be introduced into the tube is increased, however, when the viscosity is too high, the internal air of the tubular structure cannot be substituted with the solution or suspension, and the risk of disruption of the tubular structure may often occur due to the high viscosity.

This solution or suspension is mixed with dried powder or suspension of the aforementioned hollow carrier, stirred to be uniform totally, thereby allowing internal impregnation of the active ingredient into the hollow carrier followed by drying. When internal infiltration of the solution or suspension into the tubular structure is insufficient, degassing of the inside air of the tubular structure may be conducted by depressurization using a vacuum pump, an aspirator or the like. Thus, the infiltration of the solution or suspension into inside of the tubular structure can be accelerated. For the drying, the solvent may be vaporized by heating or the like. With regard to the temperature for heating then, characteristics of the encapsulated substance must be sufficiently considered. When drying at a low temperature is necessary, shortening of the time for drying can be achieved by carrying out the drying under a condition of reduced pressure. Accordingly, functional particles having a desired active ingredient substance which is encapsulated within a hollow carrier can be obtained.

With respect to the basic magnesium carbonate itself which constitutes the hollow carrier, dehydration of water of crystallization, decomposition of the hydroxyl group, and decomposition of the carbonate group are caused by heating in due order. For example, the basic magnesium carbonate of which chemical formula is $mMgCO_3.Mg(OH)_2.nH_2O$, wherein the value of n (number of water of crystallization) is 8, three to four water of crystallization is dehydrated at 50 to 100° C., thereby becoming the value of n to be 4 to 5, and further loses the water of crystallization is further lost at 100 to 250° C., leading to the value of n to be 0. When the temperature is higher than 250° C., the hydroxyl group is decomposed at 300 to 450° C., and the carbonate group is decomposed at 450 to 550° C. to discharge carbon dioxide. However, damages on the tubular structure due to these alterations are not so great. Therefore, the basic magnesium carbonate can be also modified into the anhydride or oxide by heating in a positive way, depending on the encapsulated substance or the purpose of use.

Slurry of the hollow carrier can be also used directly without recovering the dried powder. For example, for encapsulating of edible oil into the hollow carrier in a water slurry state, the edible oil is added to the water slurry of the hollow carrier comprising the basic magnesium carbonate directly or as an emulsion, and the mixture is homogenized as much as possible totally by stirring. Next, utilizing the difference between boiling points of water and edible oil, only the water is evaporated by heating this mixture. Thus, the edible oil can be encapsulated within the tubular structure.

The temperature then is not particularly limited, but may be from 40° C. to boiling point or lower under the ordinary pressure, and preferably 60 to 90° C. When the temperature is lower than 40° C., evaporation of the water requires a substantial time. Therefore, the temperature is suitably 60 to 90° C. since water can be removed in a relatively short time, but disruption of the tubular aggregated particles is not caused by boiling. Furthermore, this operation can be conducted at a lower temperature with reduced pressure, if necessary.

When the hollow carrier is subjected to a lipophilizing treatment in advenace by any one of fatty acids, resin acids and various surfactants such as coupling agents, an oily substance can be encapsulated in a comparatively easy manner. After encapsulating a desired substance in such a manner, the substance adhered to the surface of the functional particle can be eliminated by washing with a solvent such as water or alcohol, if necessary.

The functional particle thus obtained internally includes any one of the various active ingredient substance as described above, and can exert a variety of effects. Additionally, by further covering the surface thereof with an organic polymer if necessary, optimization is enabled corresponding to various use by improving the leakage preventive or protective effect of the encapsulated substance.

The organic polymer used then may be selected ad libitum depending on the use or desired performance. When a water soluble polymer which enables use of a water based solvent is used, covering can be comparatively easily executed. Examples of the water soluble polymer which may be used include starch-like substances, mannan, seaweeds, plant viscous substances, microorganism viscous substances, proteins and the like in addition to natural polymers, modified products of a natural polymer and synthetic polymers, as described above.

Covering of the particle, which internally includes effective substance within a hollow carrier, with any one of these organic polymers may be executed by allowing the internal inclusion of the effective substance followed by addition of an organic polymer in an appropriate amount prior to drying, and by drying using a fluidized bed dryer, a spray dryer, a vacuum freeze-drying dryer or the like. For a reference, these organic polymers may be used alone, or two or more kinds of the substances may be used in combination, and as the case may be, an effect which is not achieved by use alone can be also obtained by crosslinking.

The hollow carrier of the present invention comprises a tubular aggregated particle of flaky fine crystals of a basic magnesium carbonate. The functional particle can be produced according to a comparatively convenient procedure by bringing any one of various effective substances into contact with the hollow carrier to thereby encapsulate the substances within the tubular structure thereof. The unique shape that is tubular exhibits excellent characteristics such as a sustained release effect which is stable for a long time, a release-controlling effect which is a property of releasing the encapsulated substance under a specific condition, a prevention effect of degeneration in quality, a masking effect, a protective effect and the like.

The sustained release effect is also accompanied by a characteristic capable of controlling the release rate by controlling the length, internal diameter or thickness of the tube. Additionally, the aforementioned functional particle can deal with various use by covering its surface with an organic polymer to improve the leakage preventive or sustained release effect, a prevention effect of degeneration in quality, a masking effect, a protective effect or the like of the encapsulated substance, if necessary.

In addition to the filler for low density paper, low density paper, hollow carrier and functional particle described hereinabove, the tubular aggregated particle of the basic magnesium carbonate of the present invention can be utilized in various fields. Moreover, materials without formation such as fillers, pigments, paints, inks, catalyst carriers, microorganism carriers, biocarriers, plant growth regulators, olefin absorbing agents, liquid absorbing agents, oil absorbing agents, desiccating agents, aromatic agents, odor eliminating agents, sealing agents, antirusting agents, food additives, filters, filter aids, polishing agents, column packing materials, medicaments, pesticides, fertilizers and the like containing the basic magnesium carbonate of the present invention may be involved in the composition of the present invention.

In addition, the structure of the present invention is formed products in which any one of these compositions or the basic magnesium carbonate of the present invention is used. For example, rubbers, plastics, resins, papers, catalysts, various absorbing agents, heat insulating materials, noise absorbing materials, heat retaining materials, filters and the like may be involved in the structure of the present invention.

The composition or structure of the present invention is now more specifically explained. For example, the filler for use in a rubber is not only effective in weight saving of a rubber product on behalf of the characteristic which is the low bulk density as described above, but also is improved in the adhesiveness with a matrix due to the presence of irregularity in the form of a card house structure on the surface of the particle. Accordingly, it is possible to obtain a rubber product having a high strength. Also, as a filler for use in a resin, an effect such as weight saving or improvement of the strength is exerted similarly to the filler for use in a rubber, and additionally, it is also effective in imparting flame retardancy on behalf of many water molecules included within the crystal structure. Furthermore, since it is a basic magnesium carbonate, it has a halogen capturing ability as its inherent property, and has also effects in suppression of halogen release upon combustion, and suppression of deterioration of the resin which may result from free halogen.

Also, formed products or granulated products obtained through formation of the basic magnesium carbonate of the present invention using a binder or the like are not only excellent in weight saving due to the characteristic of low bulk density, but also exert effects such as heat insulating property as well as noise absorbing property, absorbency, filtrating property and the like due to the characteristic being porous. Therefore, they can be utilized as a heat insulator, a noise absorbing material, a heat retaining materials, a filter and the like.

Moreover, the functional particle of the present invention may also be included in the aforementioned composition or structure, whereby making a composition or structure with a characteristic such as a sustained release property, a release-controlling property or a masking property carried by the functional particle being utilized. For example, by including a functional particle, which has an encapsulated aromatic substance, in paper, a paper product that emits the flavor for a long time can be produced. Furthermore, by granulation of functional particles encapsulating a plant growth regulator to give granules, they can be utilized as a sustained release fertilizer from which thus encapsulated plant growth regulator is gradually released. These paper and sustained release fertilizer containing the functional particle of the present invention are also involved in the composition or structure according to the present invention.

EXAMPLES

Next, the present invention is explained more specifically with reference to Examples and Comparative Examples in which the basic magnesium carbonate is produced, and Examples and Comparative Examples of the low density paper and functional particle in which the basic magnesium carbonate is utilized. However, needless to say, the present invention is not anyhow restricted by these Examples, but specified by claims.

Example 1

Production of Basic Magnesium Carbonate According to S Method

To 2.0 L of an aqueous solution of magnesium sulfate heptahydrate (125 g/L) adjusted to be 40° C., 0.50 L of an aqueous solution of sodium carbonate anhydride (220 g/L) was gradually added while keeping the temperature at 40° C., and stirred for 50 min. to obtain a normal magnesium carbonate (first step). When the normal magnesium carbonate was observed with SEM, it was determined as being columnar particles having a diameter of 1 to 3 μm and a length of 10 to 50 μm.

Subsequently, the suspension of the columnar particles of the normal magnesium carbonate obtained in the first step (pH 10.2) was heated, and stirred for 120 min. while keeping the temperature at 55° C. to allow the production of a basic magnesium carbonate (second step). After washing thus resulting product with ion exchanged water and ethanol followed by drying, it was observed with SEM. Thus, it was determined as being aggregated particles of flaky primary particles having a thickness of 0.01 to 0.04 μm and a diameter of 0.5 to 2 μm, and as being tubular basic magnesium carbonate having an external diameter of 1 to 5 μm, an internal diameter of 0.5 to 3 μm and a length of 5 to 20 μm.

Example 2

Production of Basic Magnesium Carbonate According to S Method

A solution containing magnesium sulfate generated during the step of flue gas desulfurization according to a magnesium hydroxide method was filtrated to eliminate the solid content, and thereafter, an appropriate amount of ion exchanged water was added thereto to prepare 2.0 L of a 50 g/L magnesium sulfate solution. After adjusting the magnesium sulfate solution to be 50° C., 0.50 L of an aqueous solution of sodium carbonate (210 g/L) was gradually added thereto while keeping at the same temperature, and stirred for 20 min. to obtain a normal magnesium carbonate (first step). When this normal magnesium carbonate was observed with SEM, it was determined as being columnar particles having a diameter of 1 to 3 μm and a length of 10 to 60 μm.

After filtrating this suspension of the normal magnesium carbonate followed by washing of the solid content with ion exchanged water, the solid content was again dispersed in 2.0 L of ion exchanged water to prepare a suspension of the normal magnesium carbonate with eliminated impurities such as sodium sulfate. Subsequently, after adding an appropriate amount of an aqueous solution of sodium hydroxide to the suspension of the columnar particles of the normal magnesium carbonate obtained in the first step to adjust the pH of 10.6, the suspension was heated, and stirred for 60 min. while keeping the temperature at 70° C. to allow the production of a basic magnesium carbonate (second step).

After washing thus resulting product with ion exchanged water and ethanol followed by drying, it was observed with SEM. Thus, it was determined as being aggregated particles of flaky primary particles having a thickness of 0.01 to 0.05 μm and a diameter of 0.5 to 3 μm, and as being tubular basic magnesium carbonate having an external diameter of 2 to 3 μm, an internal diameter of 1 to 1.5 μm and a length of 10 to 20 μm.

Example 3

Production of Basic Magnesium Carbonate According to S Method

To 2.0 L of an aqueous solution of magnesium sulfate heptahydrate (125 g/L) adjusted to be 45° C., 0.50 L of an aqueous solution of sodium carbonate anhydride (220 g/L) was gradually added while keeping the temperature at 45° C., and stirred for 30 min. to obtain a normal magnesium carbonate (first step). When this normal magnesium carbonate was observed with SEM, it was determined as being columnar particles having a diameter of 1 to 3 μm and a length of 10 to 50 μm.

Subsequently, the suspension of the columnar particles of the normal magnesium carbonate obtained in the first step (pH 10.5) was heated, and stirred for 120 min. while keeping the temperature at 55° C. to allow the production of a basic magnesium carbonate (second step). After washing thus obtained product with ion exchanged water and ethanol followed by drying, it was observed with SEM. Thus, it was determined as being aggregated particles of flaky primary particles having a thickness of 0.01 to 0.04 μm and a diameter of 0.5 to 2 μm, and as being tubular basic magnesium carbonate having an external diameter of 2 to 4 μm, an internal diameter of 1 to 2 μm and a length of 5 to 20 μm.

Example 4

Production of Basic Magnesium Carbonate According to S Method

To 2.0 L of an aqueous solution of magnesium sulfate heptahydrate (125 g/L) adjusted to be 48° C., 0.50 L of an aqueous solution of sodium carbonate anhydride (225 g/L) was gradually added while keeping the temperature at 48° C., and stirred for 30 min. to obtain a normal magnesium carbonate (first step). When the normal magnesium carbonate was observed with SEM, it was determined as being columnar particles having a diameter of 1 to 2 μm and a length of 10 to 50 μm.

Subsequently, the suspension of the columnar particles of the normal magnesium carbonate obtained in the first step (pH 10.7) was heated, and stirred for 120 min. while keeping the temperature at 53° C. to allow the production of a basic magnesium carbonate (second step). After washing thus obtained product with ion exchanged water and ethanol followed by drying, it was observed with SEM. Thus, it was determined as being aggregated particles of flaky primary particles having a thickness of 0.01 to 0.04 μm and a diameter of 0.5 to 2 μm, and as being tubular basic magnesium carbonate having an external diameter of 1 to 3 μm, an internal diameter of 0.5 to 1.5 μm and a length of 5 to 20 μm.

Example 5

Production of Basic Magnesium Carbonate According to G Method

To 2.0 L of a suspension of magnesium hydroxide (30 g/L), a gas containing carbon dioxide which comprises 25% by volume of carbon dioxide and 75% by volume of air was introduced at a rate of 8.0 L/min for 30 min. while stirring and keeping the temperature of 20° C. After that, undissolved residues were eliminated to prepare a solution of magnesium hydrogen carbonate (pH 7.3) (first step).

Subsequent to this step, an appropriate amount of an aqueous solution of sodium hydroxide was added to the solution of magnesium hydrogen carbonate to adjust the liquid pH to be 8.0 accompanied by heating to elevate the liquid temperature up to 35° C. Thereafter, the mixture was stirred for 60 min. while still kept at the same temperature to prepare a suspension of a normal magnesium carbonate (second step). When the normal magnesium carbonate was observed with SEM, it was determined as being columnar particles having a diameter of 5 to 10 μm and a length of 30 to 100 μm.

Subsequently, an appropriate amount of an aqueous solution of sodium hydroxide was added to the suspension of the columnar particles of the normal magnesium carbonate to adjust the liquid pH of 10.5 accompanied by heating to elevate the liquid temperature up to 55° C. Thereafter, the mixture was stirred for 120 min. while kept at the same temperature to obtain a suspension of a basic magnesium carbonate (third step). When the basic magnesium carbonate was observed with SEM, it was determined as being tubular aggregated particles having an internal diameter of 2 to 5 μm, an external diameter of 5 to 10 μm and a length of 20 to 50 μm, comprising flaky fine crystals having a thickness of 0.02 to 0.1 μm and a diameter of 1 to 2 μm.

Example 6

Production of Basic Magnesium Carbonate According to G Method

Similarly to Example 5 except that the pH in the second step was changed to 9.0 and the temperature in the third step was changed to 50° C., a suspension of a basic magnesium carbonate was obtained.

When the normal magnesium carbonate produced in the second step was observed with SEM, it was determined as being columnar particles having a diameter of 1 to 3 μm and a length of 2.0 to 50 μm. Furthermore, when the basic magnesium carbonate obtained in the third step was observed with SEM, it was determined as being tubular aggregated particles having an internal diameter of 1 to 2 μm, an external diameter of 2 to 3 μm and a length of 5 to 30 μm, comprising flaky fine crystals having a thickness of 0.01 to 0.05 μm and a diameter of 0.2 to 1 μm.

Example 7

Production of Basic Magnesium Carbonate According to G Method

Similarly to Example 5 except that the pH in the second step was changed to 10.0 and the temperature in the third step was changed to 40° C., a suspension of a basic magnesium carbonate was obtained.

When the normal magnesium carbonate produced in the second step was observed with SEM, it was determined as being columnar particles having a diameter of 0.5 to 1 μm and a length of 10 to 50 μm. When the basic magnesium carbonate obtained in the third step was observed with SEM, it was determined as being tubular aggregated particles having an internal diameter of 0.5 to 1 μm, an external diameter of 1 to 1.5 μm and a length of 5 to 30 μm, comprising flaky fine crystals having a thickness of 0.005 to 0.02 μm and a diameter of 0.1 to 0.5 μm.

Example 8

Production of Basic Magnesium Carbonate According to G Method

To 2.0 L of a suspension of magnesium hydroxide (45 g/L), a gas containing carbon dioxide which comprises 25% by volume of carbon dioxide and 75% by volume of air was introduced at a rate of 10.0 L/min for 45 min. while stirring and keeping the suspension temperature of 15° C. After that, undissolved residues were eliminated to prepare a solution of magnesium hydrogen carbonate (pH 7.2) (first step).

Subsequent to this step, an appropriate amount of an aqueous solution of sodium hydroxide was added to the solution of magnesium hydrogen carbonate to adjust the liquid pH of 8.0, accompanied by heating to elevate the liquid temperature up to 50° C. Thereafter, the mixture was stirred for 60 min. while still kept at the same temperature. Then, the product was filtrated and again dispersed in an equal amount of tap water to prepare a suspension of a normal magnesium carbonate (second step). When the normal magnesium carbonate was observed with SEM, it was determined as being columnar particles having a diameter of 3 to 5 μm and a length of 30 to 80 μm.

Subsequently, an appropriate amount of an aqueous solution of sodium hydroxide was added to the suspension of the columnar particles of the normal magnesium carbonate to adjust the liquid pH of 11.0, accompanied by heating to elevate the liquid temperature up to 55° C. Thereafter, the mixture was stirred for 120 min. while keeped at the same temperature to obtain a suspension of a basic magnesium carbonate (third step). When the basic magnesium carbonate was observed with SEM, it was determined as being tubular aggregated particles having an internal diameter of 2 to 5 μm, an external diameter of 3 to 8 μm and a length of 20 to 50 μm, comprising flaky fine crystals having a thickness of 0.01 to 0.05 μm and a diameter of 0.5 to 1 μm.

Example 9

Production of Basic Magnesium Carbonate According to G Method

Similarly to Example 8 except that the pH in the second step was changed to 9.0, and the pH was changed to 10.5 and the temperature was changed to 50° C. in the third step, a suspension of a basic magnesium carbonate was obtained. When the normal magnesium carbonate produced in the second step was observed with SEM, it was determined as being columnar particles having a diameter of 1 to 2 μm and a length of 20 to 50 μm.

When the basic magnesium carbonate obtained in the third step was observed with SEM, it was determined as being tubular aggregated particles having an internal diameter of 1 to 2 μm, an external diameter of 2 to 3 μm and a length of 5 to 30 μm, comprising flaky fine crystals having a thickness of 0.005 to 0.02 μm and a diameter of 0.1 to 0.5 μm.

Comparative Example 1

To 2.0 L of an aqueous solution of magnesium sulfate heptahydrate (125 g/L) adjusted to be 15° C., 0.50 L of an aqueous solution of sodium carbonate anhydride (200 g/L) was gradually added while keeped at the same temperature, and thereafter, subjected to a treatment of stirring for 3 hours while keeping the mixture temperature at 15° C. to obtain a normal magnesium carbonate. When the normal magnesium carbonate was observed with SEM, it was determined as being columnar particles having a diameter of 20 to 30 μm and a length of 100 to 500 μm.

The suspension of the normal magnesium carbonate (pH 8.5) was subjected to a treatment of stirring for 125 hours while keeping the temperature at 20° C. to allow the production of a basic magnesium carbonate. After washing thus resulting product with ion exchanged water and ethanol followed by drying, it was observed with SEM. Thus, it was determined as being aggregated particles of flaky primary particles having a thickness of 0.05 to 0.5 μm and a diameter of 1 to 7 μm, and as being amorphous to elliptical basic magnesium carbonate having a diameter of 10 to 70 μm.

Comparative Example 2

To 2.0 L of an aqueous solution of magnesium sulfate heptahydrate (125 g/L) adjusted to be 80° C., 0.50 L of an aqueous solution of sodium carbonate anhydride (220 g/L) was gradually added while keeping the temperature at 80° C., and thereafter, subjected to a treatment of stirring for 60 min. while keeping the mixture temperature at 80° C. to allow the production of a basic magnesium carbonate.

After washing thus resulting product with ion exchanged water and ethanol followed by drying, it was observed with SEM. Thus, it was determined as being aggregated particles of flaky primary particles having a thickness of 0.01 to 0.05 μm and a diameter of 0.3 to 2 μm, and as being amorphous basic magnesium carbonate having a diameter of 2 to 4 μm. According to the Comparative Example, production of a normal magnesium carbonate was not determined in the reaction process.

Comparative Example 3

To 2.0 L of a suspension of magnesium hydroxide (30 g/L) adjusted to be 60° C., carbon dioxide gas was introduced at a rate of 1.5 L/min. for 240 min. while stirring and keeping the temperature of 60° C. to allow the production of a basic magnesium carbonate. According to this Comparative Example, production of a normal magnesium carbonate was not determined in the reaction process.

After washing thus obtained product with ion exchanged water and ethanol followed by drying, it was observed with SEM. Thus, it was determined as being aggregated particles of flaky primary particles having a thickness of 0.01 to 0.05 μm and a diameter of 0.5 to 2 μm, and as being elliptical to spherical basic magnesium carbonate having a diameter of 10 to 15 μm.

Comparative Example 4

To 2.0 L of a suspension of magnesium hydroxide (30 g/L), a gas containing carbon dioxide which comprises 25% by volume of carbon dioxide and 75% by volume of air was introduced at a rate of 8.0 L/min. for 30 min. while stirring and keeping the suspension temperature of 20° C. to prepare a solution of magnesium hydrogen carbonate.

Subsequently, the solution of magnesium hydrogen carbonate was heated directly (pH 7.0) to elevate the liquid temperature up to 50° C. Thereafter, the solution was stirred for 60 min. while still kept at the same temperature to prepare a suspension of a normal magnesium carbonate. When this normal magnesium carbonate was observed with SEM, it was determined as being columnar particles having a diameter of 20 to 50 μm and a length of 100 to 300 μm.

Subsequently, the suspension of columnar particles of the normal magnesium carbonate was heated directly (pH 7.8) to elevate the liquid temperature up to 85° C. Thereafter, the suspension was stirred for 180 min. while still kept at the same temperature to obtain a suspension of a basic magnesium carbonate. When the basic magnesium carbonate was observed with SEM, it was determined as being amorphous to elliptical aggregated particles of 20 to 100 μm, which comprise flaky fine crystals having a thickness of 0.05 to 0.2 μm and a diameter of 1 to 10 μm.

Evaluation of Physical Properties and the Like of Basic Magnesium Carbonate

For the basic magnesium carbonate obtained in Examples and Comparative Examples, measurement of the specific surface area according to a BET method, and measurement of fine porosimetry according to a mercury intrusion method were performed. The BET specific surface area was measured with an automated specific area calculator Macsorb (HM model-1201) produced by Mountech Co., Ltd., while the fine porosimetry was measured with a mercury intrusion type porosimeter (series 140 type, 440 type) produced by CE Instruments, respectively. The results of measurement are presented in Table 1.

Furthermore, analyses of impurities included in the basic magnesium carbonate obtained in Examples were carried out. The results are presented in Table 2.

TABLE 1

| | | | Fine porosimetry | | |
|---|---|---|---|---|---|
| | Shape of particle — | BET specific area m²/g | 0.01-100 μm Volume of fine pores (A) mm³/g | 0.5-5 μm Volume of fine pores (B) mm³/g | B/A — |
| Example 1 | tubular | 144 | 9000 | 5400 | 0.60 |
| Example 2 | tubular | 98 | 9400 | 5200 | 0.55 |
| Example 3 | tubular | 160 | 9300 | 4800 | 0.52 |
| Example 4 | tubular | 182 | 10300 | 5600 | 0.54 |
| Example 5 | tubular | 118 | 7190 | 4130 | 0.57 |
| Example 6 | tubular | 160 | 9260 | 4750 | 0.51 |

TABLE 1-continued

| | | | Fine porosimetry | | |
|---|---|---|---|---|---|
| | Shape of particle — | BET specific area m²/g | 0.01-100 μm Volume of fine pores (A) mm³/g | 0.5-5 μm Volume of fine pores (B) mm³/g | B/A — |
| Example 7 | tubular | 196 | 7440 | 3710 | 0.50 |
| Example 8 | tubular | 125 | 7700 | 4300 | 0.56 |
| Example 9 | tubular | 190 | 7650 | 4110 | 0.54 |
| Comparative Example 1 | Amorphous to elliptical | 58 | 5500 | 500 | 0.09 |
| Comparative Example 2 | Amorphous | 24 | 2800 | 1200 | 0.43 |
| Comparative Example 3 | Elliptical to spherical | 42 | 5400 | 2000 | 0.37 |
| Comparative Example 4 | Amorphous to elliptical | 48 | 4400 | 1600 | 0.36 |

TABLE 2

| | Content of impurities | |
|---|---|---|
| | Na₂O % by weight | SO₃ % by weight |
| Example 1 | 0.46 | 0.48 |
| Example 5 | 0.06 | 0.02 |
| Example 6 | 0.10 | 0.02 |
| Example 7 | 0.05 | 0.01 |
| Example 8 | 0.04 | 0.01 |
| Example 9 | 0.04 | 0.02 |

As is clear from Table 1, it is found that the basic magnesium carbonate of the present invention obtained in Examples has a great specific surface area and pore volume, and has a high ratio (B/A) of the pore volume of the pores having a pore diameter of 0.5 to 5 μm in the porosimetry.

Additionally, it is found from Table 2 that content of the impurities in the basic magnesium carbonate obtained according to the G method (Examples 5 to 9) is reduced than that in the basic magnesium carbonate obtained according to the S method (Example 1). More specifically, it can known from Table 2 that the Na₂O content in Examples 5 to 9 (G method) is a quarter or less in comparison with that in Example 1 (S method), and the SO₃ content is also 1/20 or less. Therefore, it is suggested that when production of a basic magnesium carbonate with less content of impurities is intended, the G method according to the present invention is more desired.

Utilization Examples and the Like for Filler for Low Density Paper and Low Density Paper Production of low density paper and the like is now described in which the basic magnesium carbonate and the like that was produced in Examples was used as a filler.

Utilization Example 1

To a water based slurry including 100 parts by weight of a broadleaf tree craft pulp (freeness: 211 mLcsf), 40 parts by weight of the tubular aggregated particles of the basic magnesium carbonate obtained in Example 1 as a filler for low density paper was added, followed by stirring to admix uniformly. Thereafter, an appropriate amount of an aqueous solution of polyacrylamide as a flocculating agent was added thereto, and wet paper was obtained by hand-papermaking using a square papermaking sheet machine. After compressing thus obtained wet paper with a pressing machine at a pressure of 5.0 kgf/cm², it was dried with a dram dryer of which surface temperature is 130° C. to obtain hand made paper with a weighing of 33 g/m², and a filler content of 18% by weight.

Utilization Example 2

Similarly to Utilization Example 1 except that a mixture of 35 parts by weight of the tubular aggregated particles of the basic magnesium carbonate obtained in Example 1, and 8 parts by weight of commercially available titanium oxide (anatase type, mean primary particle diameter: 0.15 μm) are used as a filler for low density paper, hand made paper was obtained.

Utilization Example 3

To a water based slurry including 100 parts by weight of broadleaf tree craft pulp (freeness: 447 mLcsf), 15 parts by weight of the tubular aggregated particles of the basic magnesium carbonate obtained in Example 1 was added as a filler for low density paper, followed by stirring to admix uniformly. Thereafter, an appropriate amount of an aqueous solution of polyacrylamide as a flocculating agent was added thereto, and wet paper was obtained by hand-papermaking using a square papermaking sheet machine. After compressing thus obtained wet paper with a pressing machine at a pressure of 5.0 kgf/cm², it was dried with a dram dryer of which surface temperature being 130° C. to obtain hand made paper with a weighing of 63 g/m², and a filler content of 8% by weight.

Utilization Comparative Example 1

To a water based slurry including 100 parts by weight of broadleaf tree craft pulp (freeness: 211 mLcsf), 40 parts by weight of synthetic calcium carbonate (spindle shaped having a major axis of 1.0 to 1.2 μm and a minor axis of 0.2 to 0.3 μm) was added as a filler, followed by stirring to admix uniformly. Thereafter, an appropriate amount of an aqueous solution of polyacrylamide as a flocculating agent was added thereto, and wet paper was obtained by hand-papermaking using a square papermaking sheet machine. After compressing thus obtained wet paper with a pressing machine at a pressure of 5.0 kgf/cm², it was dried with a dram dryer of which surface temperature being 130° C. to obtain hand made paper with a weighing of 33 g/m², and a filler content of 18% by weight.

Utilization Comparative Example 2

Similarly to Utilization Comparative Example 1 except that a mixture of 35 parts by weight of the same synthetic calcium carbonate as that used in Utilization Comparative Example 1, and 8 parts by weight of titanium oxide (anatase type, mean primary particle diameter: 0.15 μm) are used as a filler, hand made paper was obtained.

Utilization Comparative Example 3

Similarly to Utilization Comparative Example 1 except that 40 parts by weight of a commercially available basic magnesium carbonate (amorphous aggregated particles of 2 to 20 μm) was used as a filler, hand made paper was obtained.

Utilization Comparative Example 4

To a water based slurry including 100 parts by weight of broadleaf tree craft pulp (freeness: 447 mLcsf), 15 parts by weight of the same synthetic calcium carbonate as that used in Utilization Comparative Example 1 was added as a filler, followed by stirring to admix uniformly. Thereafter, an appropriate amount of an aqueous solution of polyacrylamide as a flocculating agent was added thereto, and wet paper was obtained by hand-papermaking using a square papermaking sheet machine. After compressing thus obtained wet paper with a pressing machine at a pressure of 5.0 kgf/cm², it was dried with a dram dryer of which surface temperature being 130° C. to obtain hand made paper with a weighing of 63 g/m², and a filler content of 8% by weight.

Evaluation of Hand Made Paper

For the hand made paper obtained in Utilization Examples 1 to 3 and Utilization Comparative Examples 1 to 4, evaluation tests on density and rigidity were carried out. The density was measured in accordance with JIS P 8118 (determination of paper and board for thickness and density), and the rigidity was measured in accordance with JIS P 8143 (determination of stiffness of paper with Clark stiffness testing machine) for Clark rigidity. The results of evaluation are presented in Table 3. For a reference, with regard to Clark rigidity, a greater value means higher rigidity.

TABLE 3

| | Filler | Basic weight g/m² | Filler content % by weight | Density g/m³ | Clark rigidity cm³/100 |
|---|---|---|---|---|---|
| Utilization Example 1 | Tubular aggregated particles of basic magnesium carbonate | 33.4 | 18.2 | 0.48 | 16.1 |
| Utilization Example 2 | Tubular aggregated particles of basic magnesium carbonate Titanium oxide | 33.1 | 17.9 | 0.52 | 15.1 |
| Utilization Example 3 | Tubular aggregated particles of basic magnesium carbonate | 62.9 | 7.6 | 0.52 | 58.9 |
| Utilization Comparative Example 1 | Synthetic calcium carbonate | 33.4 | 17.9 | 0.55 | 13.4 |
| Utilization Comparative Example 2 | Synthetic calcium carbonate Titanium oxide | 33.2 | 18.2 | 0.57 | 11.1 |
| Utilization Comparative Example 3 | Amorphous aggregated particle of basic magnesium carbonate | 33.4 | 18.0 | 0.54 | 14.1 |
| Utilization Comparative Example 4 | Synthetic calcium carbonate | 63.2 | 7.7 | 0.56 | 57.7 |

It is found as is clear from Table 3, that the hand made paper obtained in Utilization Examples has lower density and excellent rigidity in comparison with that according to Utilization Comparative Examples at the almost identical weighing and the identical filler content. More specifically, when Utilization Examples 1 and 2, and Utilization Comparative Examples 1 to 3 are compared in which the weighing is about 33 g/m$^2$ and the filler content is about 18% by weight in both Utilization Examples and Utilization Comparative Examples, although the density of the hand made paper in Utilization Comparative Examples is 0.54 to 0.57 g/cm$^3$ it is 0.48 to 0.52 g/cm$^3$ in Utilization Examples. Therefore, changes to the low density maximally of about 0.1 g/cm$^3$ was achieved.

Moreover, when Utilization Example 3 and Utilization Comparative Example 4 are compared in which the weighing is about 63 g/m$^2$ and the filler content is about 8% by weight, although the density of the hand made paper in Utilization Comparative Example is 0.56 g/cm$^3$, it is 0.52 g/cm$^3$ in Utilization Example. Therefore, changes to the low density by about 0.04 g/cm$^3$ was achieved.

Furthermore, the hand made paper in Examples is excellent also in rigidity. More specifically, it is found from Table 3, that when the hand made paper according to Utilization Examples is compared to the hand made paper according to Utilization Comparative Examples at the almost identical weighing and identical filler content, the former is excellent in rigidity. For example, when the hand made paper according to Utilization Example 1 is compared to that according to Utilization Comparative Example 1, it is found that Clark rigidity is 16.1 cm$^3$/100 in Utilization Example 1, while it is 13.4 cm$^3$/100 in Utilization Comparative Example 1, although the weighing and the filler content are identical in both cases. Therefore, it is suggested that the present invention is excellent in Clark rigidity.

Utilization Examples and the Like for Hollow Carrier and Functional Particle

Production of a functional particle in which the basic magnesium carbonate or the like produced in Examples is used as a carrier is now explained.

Utilization Example 4

In a 500 mL beaker, 10.0 g of the basic magnesium carbonate according to Example 1 was charged by weighing, and 200 mL of a solution of naphthalene in methanol (20 mg/mL) was added thareto, followed by soaking for one hour. After the filtration of the solid content, it was washed with methanol followed by vaporization of methanol. Accordingly, functional particles with encapsulating naphthalene were produced. In a similar manner, functional particles encapuslating naphthalene were produced also for the basic magnesium carbonate according to Examples 5 to 7.

Utilization Example 5

With 10 g of a 1% aqueous solution of alkylpolyaminoethylglycine hydrochloride, 10 g of the basic magnesium carbonate according to Example 1 was soaked. Accordingly, functional particles having a sustained release effect of alkylpolyaminoethylglycine hydrochloride was produced. In a similar manner, functional particles having a sustained release effect of alkylpolyaminoethylglycine hydrochloride were produced also for the basic magnesium carbonate according to Examples 5 to 7.

Utilization Example 6

In a 200 ml beaker, 50 g of a commercially available skipjack flavor was charged, and 50 ml of a 20% aqueous solution of a reagent α-cyclodextrin was added thereto to prepare a aqueous solution of cyclodextrin containing a skipjack flavor. To the solution, 20 g of the basic magnesium carbonate produced in Example 1 was added, followed by stirring. Then, after conducting the suction under reduced pressure until no bubble was found, drying under the ordinary condition was carried out after returning to the ordinary pressure. Thus, the skipjack flavor was encapsulated within the hollow carrier comprising the basic magnesium carbonate.

Then, 20 ml of a 2% aqueous solution of carrageenan•glucomannan crosslinked product (6:4) was added thereto, followed by admixing to give a uniform state and thereafter drying by freeze-dry lyophilization. Accordingly, functional particles encapuslating the skipjack flavor of which surface coated with a polymer (carrageenan•glucomannan crosslinked product) were produced. In a similar manner, functional particles encapsulating the skipjack flavor of which surface coated with a polymer were produced also for the basic magnesium carbonate according to Examples 5 to 7.

Utilization Example 7

In a 200 ml beaker, 10 g of commercially available bifidobacterium (freeze-dried powder product, viable cell count: 4×10$^8$/mL) and 50 ml of edible oil (manufactured by NOF Corporation, "Panacete", middle chain fatty acid ester) were mixed briefly. The basic magnesium carbonate having a tubular structure according to Example 1 was added thereto. After stirring the mixture, depressurization with a vacuum desiccator was conducted, thereby allowing the encapsulating of the edible oil containing bifidobacterium within the basic magnesium carbonate having a tubular structure.

Next, 10 g of milk calcium and 5 g of casein sodium was added to 25 ml of water, followed by sufficient stirring. Thereafter, the basic magnesium carbonate which had been encapuslated bifidobacterium previously was added thereto and mixed to give a uniform state. Thus, functional particles encapuslating bifidobacterium of which surface being covered by casein was produced by freeze-dry lyophilization. The functional particle encapuslating bifidobacterium produced in such a manner is covered by casein on its surface, and the basic magnesium carbonate neutralizes the entered gastric acid in cases of the entry of a slight amount of gastric acid. Therefore, in the oral administration, the death ratio of bifidobacterium by gastric acid can be reduced.

Utilization Comparative Example 5

Similarly to Utilization Example 4, particles soaked with naphthalene were produced using the basic magnesium carbonate according to Comparative Examples 1 to 3.

Utilization Comparative Example 6

Similarly to Utilization Example 5, particles soaked with alkylpolyaminoethylglycine hydrochloride were produced using the basic magnesium carbonate according to Comparative Examples 1 to 3.

Utilization Comparative Example 7

Similarly to Utilization Example 6, particles soaked with a skipjack flavor were produced using the basic magnesium carbonate according to Comparative Examples 1 to 3.

Evaluation of Sustained Release Property of Naphthalene

The functional particles encapuslating naphthalene produced in Utilization Example 4 and Utilization Comparative Example 5 were placed in a 40° C. thermost bath, and the residual ratio of naphthalene was measured in a time dependent manner. From the results as presented in Table 4, it is found that although approximately 20 to 30% of naphthalene remained even after 15 days in the case of Utilization Example 4 in which the hollow carrier comprising the basic magnesium carbonate having a tubular structure produced in Example 1, entire naphthalene vaporized after 5 days in the case of Utilization Comparative Example 5 in which the basic magnesium carbonate according to Comparative Examples 1 to 3 was used.

Furthermore, in view of the internal diameter of the tubular aggregated particles used as the hollow carrier and the sustained release effect of naphthalene (naphthalene residual ratio), the highest naphthalene residual ratio was exhibited for those having a small internal diameter (Example 7, internal diameter of 0.5 to 1 μm), while low naphthalene residual ratio was exhibited for those having a large internal diameter (Example 5, internal diameter of 2 to 5 μm). It is supposed that the smaller internal diameter can diminish the contact of naphthalene with the outside air, which had been encapsulated in the tubular structure of the hollow carrier. Therefore, it is suggested that control of the releasing rate naphthalene is enabled by the alteration of the internal diameter of the tubular aggregated particles.

TABLE 4

| | Basic magnesium carbonate (carrier) | Naphthalene content (% by weight) | Residual ratio of naphthalene (%) | | | Evaluation |
|---|---|---|---|---|---|---|
| | | | After 1 day | After 5 days | After 15 days | |
| Utilization Example 4 | Example 1 | 22 | 85 | 50 | 28 | Favorable |
| Utilization Example 4 | Example 5 | 19 | 88 | 42 | 21 | Favorable |
| Utilization Example 4 | Example 6 | 29 | 83 | 49 | 24 | Favorable |
| Utilization Example 4 | Example 7 | 35 | 85 | 54 | 31 | Favorable |
| Utilization Comparative Example 5 | Comparative Example 1 | 12 | 13 | 0 | 0 | Unfavorable |
| Utilization Comparative Example 5 | Comparative Example 2 | 9 | 9 | 0 | 0 | Unfavorable |
| Utilization Comparative Example 5 | Comparative Example 3 | 19 | 19 | 0 | 0 | Unfavorable |

Evaluation of Mold Preventing Property

The following test was performed in order to evaluate the mold preventing property of the functional particles soaked with alkylpolyaminoethylglycine hydrochloride, which were produced in Utilization Example 5 and Utilization Comparative Example 6, and the basic magnesium carbonate particles according to Comparative Example 1 without soaked alkylpolyaminoethylglycine hydrochloride.

More specifically, water was poured into a lower part of a glass desiccator, and the aforementioned particles were spread on a petri dish which was placed on a middle stand. Thereon was laid a No. 5C filter paper, and then a piece of loaf-shaped bread cut into 3 cm square having a thickness of 1.2 cm was further placed thereon. The cover is in a state opened by 10%, and stored in an incubator set to be 28° C. Thereafter, presence/absence of generation of a mold on the loaf-shaped bread was determined after 30 days, after 90 days and after 120 days.

The results are as shown in Table 5. Generation of a mold was not found for the functional particles produced in Utilization Example 5 in which the basic magnesium carbonate comprising a tubular structure was used as a hollow carrier even after 120 days. On the other hand, with regard to the functional particles according to Utilization Comparative Example 6 in which the basic magnesium carbonate according to Comparative Examples 1 to 3 was used, generation of a mold was found since 90 days after. Furthermore, for the basic magnesium carbonate without soaked alkylpolyaminoethylglycine hydrochloride according to Comparative Example, a large amount of molds were generated after 30 days.

TABLE 5

| | Basic magnesium carbonate (Carrier) | Presence/absence of mold | | | Evaluation |
|---|---|---|---|---|---|
| | | After 30 days | After 90 days | After 120 days | |
| Utilization Example 5 | Example 1 | Absent | Absent | Absent | Favorable |
| Utilization Example 5 | Example 5 | Absent | Absent | Absent | Favorable |
| Utilization Example 5 | Example 6 | Absent | Absent | Absent | Favorable |
| Utilization Example 5 | Example 7 | Absent | Absent | Absent | Favorable |
| Utilization Comparative Example 6 | Comparative Example 1 | Absent | Present | Present | Unfavorable |
| Utilization Comparative Example 6 | Comparative Example 2 | Absent | Present | Present | Unfavorable |
| Utilization Comparative Example 6 | Comparative Example 3 | Absent | Present | Present | Unfavorable |
| Unsoaked basic magnesium carbonate (Comparative Example 1) | | Present | Present | Present | Unfavorable |

Evaluation of Masking Effect of Skipjack Flavor

Each 10 gram of functional particles internally including a skipjack flavor produced in Utilization Example 6 and Utilization Comparative Example 7 was charged in six 200 ml beakers, respectively, and each 6.2 gram of a commercially available skipjack flavor was charged in other six 200 ml beakers, respectively by weighing. Then, they were stored in a room with constant temperature and humidity at room temperature of 23° C. and humidity of 50%. Hot water in an amount of 100 ml was poured into the beaker on the initiation date of the test, after 3 days, after 1 week, after 2 weeks, after 1 month and after 2 months, and the intensity of the flavor was determined.

The results are as shown in Table 6. The functional particles encapsulating a skipjack flavor according to Utilization Example 6 were determined to emit a strong flavor even after 2 months. On the other hand, with regard to the functional particles according to Utilization Comparative Example 7 in which the basic magnesium carbonate according to Comparative Examples 1 to 3 was used, the flavor was attenuated after 1 week, and almost no flavor was felt after 2 weeks. Moreover, with regard to the commercially available skipjack flavor, the flavor was attenuated after 3 days, and almost no flavor was felt after 1 week.

TABLE 6

| | Basic magnesium carbonate (carrier) | Intensity of flavor | | | | | |
|---|---|---|---|---|---|---|---|
| | | Initiation date | After 3 days | After 1 week | After 2 weeks | After 1 month | After 2 months |
| Utilization Example 6 | Example 1 | ◎ | ◎ | ◎ | ◎ | ◎ | ◎ |
| Utilization Example 6 | Example 5 | ◎ | ◎ | ◎ | ◎ | ◎ | ◎ |
| Utilization Example 6 | Example 6 | ◎ | ◎ | ◎ | ◎ | ◎ | ◎ |
| Utilization Example 6 | Example 7 | ◎ | ◎ | ◎ | ◎ | ◎ | ◎ |
| Utilization Comparative Example 7 | Comparative Example 1 | ◎ | ○ | Δ | X | X | X |
| Utilization Comparative Example 7 | Comparative Example 2 | ◎ | ○ | Δ | X | X | X |
| Utilization Comparative Example 7 | Comparative Example 3 | ◎ | ○ | Δ | X | X | X |
| Commercially available skipjack flavor (without carrier) | | ◎ | Δ | X | X | X | X |

◎: strong,
○: normal,
Δ: weak,
X: almost absent

As is clear from the results hereinabove, namely from Tables 4 to 6, it is found that the functional particles according to Utilization Examples have a high sustained release property and a masking effect, derived from the unique shape of the hollow carrier comprising the tubular aggregated particle of flaky fine crystals of the basic magnesium carbonate.

INDUSTRIAL APPLICABILITY

The present invention provides a basic magnesium carbonate having the novel and unique structure as described above, a method of for producing the same and a composition or structure containing the basic magnesium carbonate. Furthermore, the present invention provides a hollow carrier and a functional particle containing the basic magnesium carbonate, and a method for producing the same. Moreover, the present invention provides a filler for low density paper, low density paper containing the basic magnesium carbonate, and a method of producing the same.

The basic magnesium carbonate of the present invention exhibits a unique shape which is porous and tubular of flaky fine crystals, and a variety of excellent characteristics derived from the shape such as high specific surface area, high pore volume, high oil absorbing property, high water absorbing property and low bulk density. The present invention provides a method for producing the basic magnesium carbonate having this excellent characteristic, and in particular, the present invention also provides a method capable of producing this basic magnesium carbonate at a low cost and with a low content of impurities.

Furthermore, the composition or structure of the present invention is any one of various compositions and structures containing the basic magnesium carbonate, such as rubbers, resins, paper, formed products, medical or agricultural drugs and cosmetics, whereby enabling the aforementioned characteristic to impart to various products.

On behalf of the shape that is tubular and the irregularity on the particle surface, it exerts a reinforcement effect in utilization as various fillers, and is also effective in weight saving of products which are to include the same, on behalf of the characteristic of low bulk density, derived from the tubular shape. Additionally, on behalf of the shape which is tubular and the feature of being an aggregated particle in the form of a card house structure, it is also excellent in the performance as a porous material, and is also effective as various adsorbing agents and carriers.

The functional particle of the present invention can be produced by a relatively simple process by bringing a hollow carrier comprising a tubular aggregated particle of flaky fine crystals of the basic magnesium carbonate into contact with any one of various active ingredients to thereby encapsulate those ingredients within the tubular structure. According to the present invention, excellent characteristics such as a sustained release effect which is stable for a long time, a release-controlling effect which is a property of releasing the encapsulated substance under a specific condition, a prevention effect of degeneration in quality, a masking effect and a protective effect are exerted on behalf of the unique shape that is tubular. Particularly, in connection with the sustained release effect, it also has an excellent character capable of regulating the velocity of release of the same by controlling the length, internal diameter or thickness of the tube.

Additionally, the filler for low density paper of the present invention is a composition containing the basic magnesium carbonate, and the low density paper of the present invention contains it as a filler. The low density paper is not only the paper having lower density in comparison with the paper containing only a generally employed filler such as calcium carbonate, kaolin and titanium oxide, but can suppress the deterioration of rigidity which was raised as a problem in saving weight of paper.

The invention claimed is:

1. A basic magnesium carbonate comprising a tubular aggregated particle of flaky fine crystals, wherein the tubular aggregated particle has a hollow structure and said basic magnesium carbonate has hydroxyl group and water of crystallization and is represented by the formula $mMgCO_3 \cdot Mg(OH)_2 \cdot nH_2O$, where m is 3 to 5 and n is 3 to 8.

2. The basic magnesium carbonate according to claim 1, wherein the tubular aggregated particle has an internal diameter of 0.5 to 5 μm, an external diameter of 1 to 20 μm, a length of 5 to 200 μm and a ratio of length/external diameter of 2 to 50.

3. The basic magnesium carbonate according to claim 1 or 2, which has a specific surface area of 70 to 200 $m^2/g$ according to a BET method.

4. The basic magnesium carbonate according to claim 1, wherein said basic magnesium carbonate comprises pores and wherein a pore volume (A) of pores having a pore diameter of 0.01 to 100 μm is 5000 to 12000 $mm^3/g$, and a ratio B/A which is a ratio of the pore volume (A) to a pore volume (B) of pores having a pore diameter of 0.5 to 5 μm is 0.45 to 0.85, in the porosimetry measured by a mercury intrusion method.

5. A method for producing a basic magnesium carbonate comprising a tubular aggregated particle of flaky fine crystals, wherein the tubular aggregated particle has a hollow structure, which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

6. The method for producing a basic magnesium carbonate according to claim 5, wherein an aqueous solution containing magnesium sulfate which is generated in a desulfurization and neutralization step by reaction of an exhaust gas with magnesium hydroxide is utilized as the water soluble magnesium salt in the first step.

7. The method for producing a basic magnesium carbonate according to claim 5 or 6, wherein the columnar particle of the normal magnesium carbonate produced in the first step has a diameter of 0.5 to 10 μm and a length of 5 to 500 μm.

8. The method for producing a basic magnesium carbonate according to claim 5, wherein the heat treatment of the suspension of the columnar particles of the normal magnesium carbonate in the second step is conducted at a pH of 7.5 to 11.5.

9. A method for producing a basic magnesium carbonate comprising a tubular aggregated particle of flaky fine crystals, wherein the tubular aggregated particle has a hollow structure, which comprises a first step of introducing a gas containing carbon dioxide into a suspension of magnesium hydroxide to prepare a solution of magnesium hydrogen carbonate, a second step of adjusting the solution of magnesium hydrogen carbonate to have a pH of 7.5 to 11.0 to produce a columnar particle of a normal magnesium carbonate, and a third step of adjusting a suspension of the columnar particles of the normal magnesium carbonate to have a pH of 9.0 to 12.0 and a temperature in a range of 30 to 75° C., followed by keeping the temperature within the range to produce a basic magnesium carbonate.

10. The method for producing a basic magnesium carbonate according to claim 9, wherein the solution of magnesium hydrogen carbonate is prepared by introducing a gas containing carbon dioxide into a suspension of magnesium hydroxide which is kept at 35° C. or lower in the first step.

11. The method of producing a basic magnesium carbonate according to claim 9 or 10, wherein the temperature in the production of the columnar particle of the normal magnesium carbonate from the solution of magnesium hydrogen carbonate is set to be 20 to 55° C. in the second step.

12. The method for producing a basic magnesium carbonate according to claim 9, wherein the columnar particle of the normal magnesium carbonate having a diameter of 0.5 to 10 μm and a length of 5 to 500 μm is produced in the second step.

13. The method for producing a basic magnesium carbonate according to claim 9, wherein the pH in the production of the basic magnesium carbonate from the suspension of columnar particles of the normal magnesium carbonate in the third step is set to be higher than the pH in the production of the normal magnesium carbonate in the second step.

14. The method for producing a basic magnesium carbonate according to claim 9, wherein the tubular aggregated particle of the basic magnesium carbonate having a desired diameter and/or length is produced in the third step, by altering the diameter and/or length of the columnar particle of the normal magnesium carbonate through regulating the pH and/or temperature in the production of the normal magnesium carbonate in the second step.

15. A filler for low density paper which comprises the basic magnesium carbonate according to claim 1, or the basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

16. A low density paper which comprises the basic magnesium carbonate according to claim 1, or a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C., as a filler.

17. The low density paper according to claim 16, wherein the content of the basic magnesium carbonate is 2 to 25% by weight per absolute dry weight of the paper.

18. The low density paper according to claim 16 or 17, which has a weighing of 25 to 75 g/m², wherein the filler is included in an amount of 5 to 25% by weight per absolute dry weight of the paper, and 20 to 100% by weight of the basic magnesium carbonate is included in the filler.

19. The low density paper according to claim 16, which has a density of 0.40 to 0.55 g/cm³.

20. A method for producing a low density paper which comprises the papermaking through blending the basic magnesium carbonate according to claim 1, or a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C., as a filler.

21. A hollow carrier which comprises the basic magnesium carbonate according to claim 1, or a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

22. A functional particle which comprises one or more substances encapsulated within a hollow carrier comprising the basic magnesium carbonate according to claim 1, or a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

23. The functional particle according to claim 22, wherein a surface of the hollow carrier encapsulating the one or more substances is covered by a polymer substance.

24. The functional particle according to claim 22 or 23, wherein the encapsulated substance is an aromatic substance, a nutritional agent, a food additive, medicament, pesticide or fertilizer.

25. A method for preparing a functional particle, which comprises encapsulating one or more substances within a hollow carrier comprising the basic magnesium carbonate according to claim 1, or encapsulating the one or more substances within a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

26. A method for preparing a functional particle, which comprises encapsulating one or more substances within a hollow carrier comprising the basic magnesium carbonate according to claim 1, or encapsulating the one or more substances within a basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C., followed by covering a surface of the functional particle with a polymer substance.

27. The method of preparing a functional particle according to claim 25 or 26, wherein a substance to be encapsulated in a hollow carrier is at least one selected from the group consisting of an aromatic substance, a nutritional agent, a food additive, medicament, pesticide and fertilizer.

28. A composition or structure which comprises the basic magnesium carbonate according to claim 1.

29. A composition or structure which comprises the basic magnesium carbonate according to claim 1, produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

30. A composition or structure which comprises the basic magnesium carbonate according to claim 1, a functional particle which comprises one or more substances encapsulated within a hollow carrier comprising a basic magnesium carbonate, or the basic magnesium carbonate produced by a production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

31. A composition or structure which comprises the basic magnesium carbonate according to claim 1, or a functional particle produced by a production method which comprises bringing a hollow carrier into contact with one or more substances to thereby encapsulate the substances within the hollow carrier comprising the basic magnesium carbonate or the basic magnesium carbonate produced by the production method which comprises a first step of mixing a water soluble magnesium salt and a water soluble carbonate salt in an aqueous solution to produce a columnar particle of a normal magnesium carbonate at a temperature of 20 to 60° C., and a second step of subjecting a suspension of the columnar particles of the normal magnesium carbonate to a heat treatment at a higher temperature than the temperature in the production of the normal magnesium carbonate in the first step, and at a temperature of 35 to 80° C.

* * * * *